United States Patent [19]

Bergmann et al.

[11] Patent Number: 4,898,868
[45] Date of Patent: Feb. 6, 1990

[54] 3-DEMETHYL-4-FLUOROMEVALONIC ACID DERIVATIVES, A PROCESS FOR THE PREPARATION THEREOF, PHARMACEUTICAL PRODUCTS BASED ON THESE COMPOUNDS, THE USE THEREOF, AND INTERMEDIATES

[75] Inventors: Andreas Bergmann, Frankfurt am Main; Wilhelm Bartmann, Bad Soden am Taunus; Gerhard Beck, Frankfurt am Main; Hans-Hermann Lau, Bad Soden am Taunus, all of Fed. Rep. of Germany

[73] Assignee: Hoechst Aktiengesellschaft, Frankfurt am Main, Fed. Rep. of Germany

[21] Appl. No.: 216,752

[22] Filed: Jul. 8, 1988

[30] Foreign Application Priority Data

Jul. 10, 1987 [DE] Fed. Rep. of Germany ....... 3722809

[51] Int. Cl.$^4$ .................... A61K 31/44; C07D 213/35; C07D 405/06
[52] U.S. Cl. .................................. 514/277; 514/256; 514/336; 514/422; 514/427; 514/438; 514/444; 514/460; 514/461; 514/568; 544/335; 546/268; 546/342; 548/517; 549/60; 549/79; 549/292; 549/501
[58] Field of Search ................ 546/342, 268; 514/277, 514/336; 549/292

[56] References Cited

U.S. PATENT DOCUMENTS 4,657,918  4/1987  Findlay et al. ................. 546/268
4,812,460  3/1989  Lazer ............................. 514/277

FOREIGN PATENT DOCUMENTS

0142146A2  5/1985  European Pat. Off. .
179559     4/1986  European Pat. Off. .
216127     4/1987  European Pat. Off. .
217092     4/1987  European Pat. Off. .
3530797A1  3/1987  Fed. Rep. of Germany .
3530798A1  3/1987  Fed. Rep. of Germany .
3632893A1  4/1988  Fed. Rep. of Germany .
2392016   12/1978  France .
3303968   12/1988  Japan ............................... 546/342

OTHER PUBLICATIONS

Endo et al.; "ML-236A, ML-236B, and ML-236C, New Inhibitors of Cholesterogenesis Produced by Penicillium Citrinum"; The Journal of Antibiotics; vol. XXIX No. 12; (1976); pp. 1346-1348.

Brown et al.; "Crystal and Molecular Structure of Compactin, a New Antifungal Metabolite from Penicillium brevicompactum"; J.C.S., Perkins, I; (1976); pp. 1165-1170.

Stokker et al.; "Synthesis and X-Ray Characterization of 6(S)-Epi-Mevinolin, a Lactone Epimer", J. Org. Chem.; (1986); vol. 51; pp. 4931-4934.

Primary Examiner—Glennon H. Hollrah
Attorney, Agent, or Firm—Finnegan, Henderson, Farabow, Garrett and Dunner

[57] ABSTRACT

3-Demethyl-4-fluoromevalonic acid derivatives, a process for the preparation thereof, pharmaceutical products based on these compounds, the use thereof, and intermediates 3-Demethyl-4-fluoromevalonic acid derivatives of the formula I, and the corresponding dihydroxy carboxylic acid derivatives of the formula II

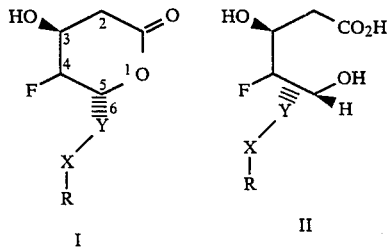

in which R, X and Y have the stated meanings, processes for the preparation of these compounds, the use thereof as medicaments, and pharmaceutical products are described. In addition, new intermediates for the preparation of the compounds of the formula I and formula II are described.

3 Claims, No Drawings

3-DEMETHYL-4-FLUOROMEVALONIC ACID DERIVATIVES, A PROCESS FOR THE PREPARATION THEREOF, PHARMACEUTICAL PRODUCTS BASED ON THESE COMPOUNDS, THE USE THEREOF, AND INTERMEDIATES

DESCRIPTION

Hypercholesterolemia is one of the essential primary risk factors for one of the commonest cardiovascular disorders, atherosclerosis (Kennel et al., Am. Intern. Med. 74 (1971), 1). Influencing the activity of the key enzyme of human cholesterol biosynthesis, HMG-CoA reductase, it thus nowadays regarded as a rational way of discovering new medicaments for the treatment of atherosclerosis.

In 1976, Endo et al. (J. Antibiotics, 29, (1976) 1346) and Brown et al. (J. Chem. Soc. Perkin I 1976, 1165) found a potent competitive inhibitor of HMG-CoA reductase in the culture broths of microorganisms, called compactin, a derivative of 3-demethylmevalonic acid. German Offenlegungsschrift 3,530,798 (corresponds to EP-A 0,216,127; U.S. patent application Ser. No. 900,848) describes compactin derivatives which carry phenoxy radicals substituted in the 6 position. German Offenlegungsschrift 3,530,797 (corresponds to EP-A 0,217,092; U.S. patent application Ser. No. 900,887) describes compactin derivatives which carry benzyl or benzylidene radicals suitably substituted in the 6 position, and the free carboxylic acids, esters and salts thereof. German Offenlegungsschrift 3,632,893 proposes compactin derivatives which are linked at C-6 to substituted thiophenoxy, and the sulfoxides and sulfones thereof, as inhibitors of HMG-CoA reductase.

Although it is known that slight changes in the substitution pattern of the compactin lactone skeleton may result in drastic decreases in the inhibitory effect on HMG-CoA reductase (for example Stokker et al., J. Org. Chem 51 (1986) 4931, or European patent application No. 0,142,146), we have now found, surprisingly, that, in the case of compactin analogs which have a fluorine atom in the 4 position of the lactone skeleton, these compounds have a potent inhibitory effect on cholesterol biosynthesis.

Hence the present invention relates to 3-demethyl-4-fluoromevalonic acid derivatives of the general formula I

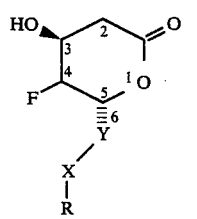

(I)

and to the corresponding free dihydroxy carboxylic acids of the formula II

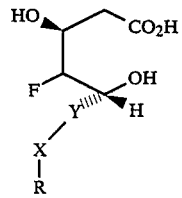

(II)

and to the pharmaceutically utilizable salts and esters thereof. In formula I or II, Y-X-R denotes (A) the group of the formula

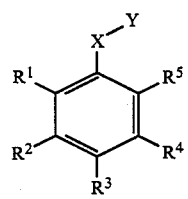

(III)

in which
Y-X is the $CH_2$) or $CH_2S$ group, and
$R^1$ and $R^5$ are identical or different and denote (a) hydrogen or halogen, (b) cycloalkyl having 4–4 carbon atoms or a phenyl radical which can be substituted in the nucleus 1 to 3 times by halogen, trifluoromethyl and/or alkyl or alkoxy, each having 1–4 carbon atoms, or (c) a straight-chain or branched alkyl radical having 1 to 18 carbon atoms or a straight-chain or branched alkenyl radical having 2 to 18 carbon atoms, it being possible for the alkyl and alkenyl radicals in turn to be substituted 1–3 times by (α) straight-chain or branched alkoxy radicals having up to 10 carbon atoms, or cycloalkoxy radicals having 3 to 7 carbon atoms, or straight-chain or branched alkenyloxy or alkynyloxy radicals having 3 to 6 carbon atoms, (β) halogen, hydroxyl, cycloalkyl having 3–7 carbon atoms, unsubstituted phenyl or α- or β-thienyl radicals, or phenyl or α- or β-thienyl radicals which in turn are substituted in the nucleus 1 to 3 times by halogen, trifluoromethyl and/or alkyl or alkoxy having 1 to 4 carbon atoms, (γ) unsubstituted phenoxy, benzyloxy, or α- or β-thienyloxy radicals, or phenoxy, benzyloxy or α- or β-thienyloxy radicals which in turn are substituted in the nucleus 1 to 3 times by halogen, trifluoromethyl and/or alkyl or alkoxy having 1 to 4 carbon atoms, (δ) the group

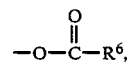

where $R^6$ denotes: a straight-chain or branched alkyl or alkenyl radical having up to 8 carbon atoms, or a cycloalkyl or cycloalkenyl radical, each of which has 3–8 carbon atoms, or an unsubstituted phenyl radical, or a phenyl radical which in turn is substituted in the nucleus 1 to 3 times by halogen, trifluoromethyl and/or alkyl or alkoxy having 1–4 carbon atoms, or a 3-pyridyl radical, $R^2$ and $R^4$ are identical or different and denote hydrogen, alkyl having 1–4 carbon atoms, halogen or alkoxy having 1–4 carbon atoms, and $R^3$ denotes hydrogen, halogen, alkyl or alkenyl having up to 4 carbon atoms, alkoxy having 1–4 carbon atoms, or phenyl which can be substituted 1–3 times by halogen or C1–C4 alkyl, (B) the group of the formula IV

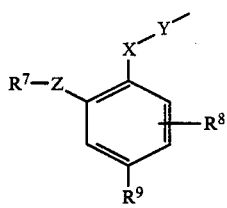

in which
X-Y is equal to CH=CH or CH$_2$—CH$_2$,
Z represents a single bond or CH$_2$, and
R$^7$ denotes a cycloaliphatic hydrocarbon radical having 3 to 7 carbon atoms, a phenyl radical which can be substituted in the nucleus 1 to 3 times by halogen, trifluoromethyl, alkyl or alkoxy, each having 1 to 6 carbon atoms, or by hydroxymethyl, or denotes a furyl, thienyl or pyridyl radical, it being possible for the heteroaromatic radicals to be substituted 1 to 2 times by halogen, trifluoromethyl, alkyl or alkoxy, each having 1 to 6 carbon atoms, and
R$^8$ and R$^9$ denote hydrogen, halogen, trifluoromethyl, or alkyl or alkoxy, each having 1 to 6 carbon atoms, (C) the group of the formula V

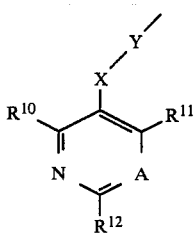

in which
X-Y is equal to CH=CH or CH$_2$—CH$_2$
A is equal to CH or N, and
R$^{10}$ denotes H, straight-chain C$_1$–C$_4$-alkyl, branched C$_3$–C$_6$-alkyl, trifluoromethyl or perfluoroisopropyl,
R$^{11}$ denotes H, straight-chain C$_1$–C$_4$-alkyl, branched C$_3$–C$_6$-alkyl, cycloalkyl having 5–8 ring carbon atoms, phenyl which can be substituted 1 or 2 times by straight-chain C$_1$–C$_3$-alkyl, C$_1$–C$_3$-alkoxy, halogen or by trifluoromethyl;
R$^{12}$ denotes H, straight-chain C$_1$–C$_4$-alkyl, branched C$_3$–C$_6$-alkyl, cycloalkyl having 5–8 ring carbon atoms, phenyl which can in turn be substituted 1 or 2 times by straight-chain C$_1$–C$_3$-alkyl, trifluoromethyl, hydroxyl or by halogen, (D) the group of the formula VI

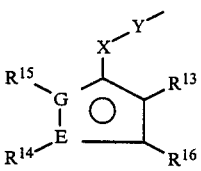

in which

X-Y is the CH=CH or CH$_2$—CH$_2$ group
G-E denotes the following sequences of atoms
(a) N—C (1H-pyrol-2-yl)
(b) S—C (2-thienyl)
(c) C—N (1H-pyrrol-3-yl)
(d) C—O (3-furyl)
(e) C—S (3-thienyl)

R$^{13}$ denotes H, straight-chain C$_1$–C$_4$-alkyl, branched C$_3$–C$_6$-alkyl, trifluoromethyl, halogen or phenyl which is optionally substituted 1–2 times by fluorine, chlorine or methyl,
R$^{14}$ denotes H, straight-chain C$_1$–C$_4$-alkyl, branched C$_3$–C$_6$-alkyl, trifluoromethyl, halogen or phenyl,
R$^{15}$ denotes H, cycloalkyl having 5–8 ring carbon atoms, branched C$_3$–C$_6$-alkyl, or phenyl which can in turn be substituted 1–2 times by straight-chain C$_1$–C$_3$-alkyl, halogen or trifluoromethyl, and
R$^{16}$ denotes H straight-chain C$_1$–C$_3$-alkyl, branched C$_3$–C$_6$-alkyl, cycloalkyl having 5–8 ring carbon atoms, trifluoromethyl, or phenyl which can in turn be substituted 1–2 times by straight-chain C$_1$–C$_3$-alkyl, halogen or trifluoromethyl, and
R$^{14}$ and R$^{16}$ together also denote a conjugated unsaturated radical having 4 carbon atoms, so that R$^{14}$ and R$^{16}$ form a fused-on aromatic system.

The substituents R$^{14}$ and R$^{15}$ are absent from those heteroaromatic compounds which have oxygen or sulfur in the corresponding positions.

The invention relates to the pure enantiomers with the absolute configuration 3S, 4R or 4S, 5R indicated in the general formula I, with the open-chain carboxylic acids of the formula II which can be obtained therefrom, and the esters and salts thereof, having the same absolute configuration.

Pharmacologically tolerated salts of the appropriate dihydroxy carboxylic acids of the general formula II which may be mentioned are alkali metal salts or ammonium salts; examples of pharmaceutically acceptable esters are alkyl esters having 1 to 4 carbon atoms, phenyl esters, benzyl esters or else 2,3-dihydroxypropyl esters.

(A) If Y-X-R denotes the group of the formula III, the substituents preferably have the following meanings:
X-Y equal to OCH$_2$ or S—CH$_2$
R$^1$ and R$^5$, identical or different:
(a) hydrogen or halogen,
(b) cycloalkyl having 5 to 6 carbon atoms, phenyl which can be substituted in the nucleus 1–3 times by halogen, trifluoromethyl and/or alkyl or alkyloxy, each having 1–4 carbon atoms, or
(c)
1. straight-chain or branched alkyl or alkoxy having up to 12 carbon atoms, it being possible for the alkyl or alkenyl radical in turn to be substituted 1–2 times by phenyl radicals which, in turn, can be substituted in the nucleus 1 to 3 times by halogen, trifluoromethyl and/or alkyl or alkoxy having 1–4 carbon atoms,
2. straight-chain alkyl substituted by

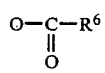

of the formula

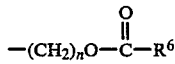

in which n denotes 1 to 3, and $R^6$ denotes a straight-chain or branched alkyl or alkenyl radical having up to 8 carbon atoms, a cycloalkyl radical having 5 to 6 carbon atoms, or a phenyl radical which in turn can be substituted in the nucleus 1-3 times by halogen, trifluoromethyl and/or alkyl or alkoxy having 1 to 4 carbon atoms, 3. straight-chain alkyl substituted by $OR^{17}$, of the formula

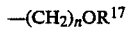

in which n denotes 1 to 3, and $R^{17}$ denotes hydrogen or a straight-chain or branched alkyl or alkenyl radical having up to 8 carbon atoms, a cycloalkyl radical having 5 to 6 carbon atoms or a phenyl radical or benzyl radical, each of which can in turn be substituted in the aromatic nucleus 1-3 times by halogen, trifluoromethyl and/or alkyl or alkoxy having 1 to 4 carbon atoms, $R^2$ and $R^4$ hydrogen, $R^3$ hydrogen, methyl, ethyl, propyl, isopropyl, t-butyl, 1-propenyl, allyl, fluorine or chlorine.

The particularly preferred meanings of the substituents are:

X-Y=$OCH_2$ or $SCH_2$ $R^1$ and $R^5$, with $R^1$ and $R^5$ being identical or different:

(1) hydrogen, methyl, ethyl, propyl, allyl, 1-propenyl, t-butyl, isopropenyl, isopropyl, cyclopentyl, cyclohexyl, p-fluorophenyl, p-chlorophenyl, 3-methyl-4-fluorophenyl (2) the group

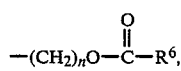

with n=1-3, where $R^6$ denotes: methyl, ethyl, propyl, i-propyl, n-butyl, i-butyl, t-butyl, phenyl or phenyl which is substituted in the nucleus 1 to 3 times by halogen, methyl or methoxy, or (3) the group $-(CH_2)_nOR^{17}$, with n=1 to 3, where $R^{17}$ denotes: hydrogen, methyl, straight-chain or branched alkyl or alkenyl having 3 to 5 carbon atoms, cyclopentyl, cyclohexyl; phenyl or benzyl, it being possible for the aromatic nuclei to be substituted 1 to 3 times by fluorine, chlorine, methyl or methoxy or (4) an alkyl group of the formula

in which m is 0 to 2, and $R^{18}$ and $R^{19}$ are identical or different and denote hydrogen, methyl, ethyl, propyl, allyl, i-propyl, n-butyl, i-butyl, t-butyl, cyclohexyl, cyclopentyl, benzyl or phenyl, it being possible for the aromatic nuclei to be substituted 1 to 3 times by fluorine, chlorine, methyl or methoxy, $R^2$ and $R^4$ hydrogen $R^3$ hydrogen, methyl, chlorine, fluorine or p-fluorophenyl.

(B) If Y-X-R denotes the group of the formula IV, the substituents preferably have the following meanings:

X-Y: CH=CH or $CH_2$—$CH_2$, Z=single bond $R^7$: cyclopentyl, cyclohexyl or a phenyl radical which can be substituted in the nucleus 1 to 3 times by halogen, trifluoromethyl, hydroxymethyl, alkyl or alkoxy, each having 1 to 4 carbon atoms, a furyl, thienyl or pyridyl radical, it being possible for the heteroaromatic radicals to be substituted 1 to 2 times by halogen, trifluoromethyl, alkyl or alkoxy, each having 1 to 4 carbon atoms, $R^8$, $R^9$: hydrogen, halogen, trifluoromethyl, alkyl or alkoxy, each having 1 to 4 carbon atoms.

Among the substituents $R^7$, those listed below are particularly preferred:

cyclopentyl, cyclohexyl or an unsubstituted phenyl radical, or phenyl which is substituted once or 3 times by halogen, trifluoromethyl, hydroxymethyl, $C_1$-$C_4$-alkyl or $C_1$-$C_4$-alkoxy, or a furyl, thienyl or pyridyl radical, it being possible for the heteroaromatic radicals to be substituted once or 2 times by halogen, trifluoromethyl, $C_1$-$C_4$-alkyl or $C_1$-$C_4$-alkoxy, especially the radicals:

cyclopentyl, cyclohexyl, phenyl, 4-chlorophenyl, 2-chlorophenyl, 3-chlorophenyl, 4-bromophenyl, 4-fluorophenyl, 4-methylphenyl, 3-trifluoromethylphenyl, 4-trifluoromethylphenyl, 4-methoxyphenyl, 3-methoxyphenyl, 3-methylphenyl, 3,4,5-trimethoxyphenyl, 3-furyl, 2-furyl, 2-thienyl, 3-thienyl, 3-pyridyl, 4-pyridyl, 2,6-dimethyl-4-pyridyl, 3-hydroxymethylphenyl, 3-ethylphenyl, 3-isopropylphenyl, 3-isobutylphenyl, 3-tert.-butylphenyl, 2-chloro-3-thienyl.

Among the substituents $R^8$ and $R^9$, those particularly preferred are:

hydrogen, 2-methyl, 2-trifluoromethyl, 2,4-dimethyl, 2,4-bistrifluoromethyl, 2-ethyl, 2-isopropyl, 2-isobutyl, 2-chloro, 2-fluoro, 2-bromo, 2,4-dichloro. 2,4-difluoro, 2-methoxy, 4-methoxy, 2,4-dimethoxy.

(C) If Y-X-R denotes the group of the formula V, those among the substituents which are preferred are:

X-Y equal to CH=CH or $CH_2$—$CH_2$, A equal to CH or N $R^{10}$: H, halogen, trifluoromethyl, straight-chain alkyl having 1 to 4 carbon atoms and branched alkyl having 3 to 4 carbon atoms.

$R^{11}$: cyclopentyl, cyclohexyl, or phenyl which can be substituted 1 or 2 times by fluorine, chlorine, straight-chain $C_1$—$C_3$-alkyl or trifluoromethyl.

$R^{12}$: methyl, branched $C_3$—$C_5$-alkyl, cyclopentyl, cyclohexyl or phenyl which can in turn be substituted 1 or 2 times by methyl, trifluoromethyl, chlorine or fluorine.

Among the substituents $R^{10}$, those particularly preferred are: methyl, isopropyl, trifluoromethyl, chlorine and fluorine.

Among the substituents $R^{11}$, those particularly preferred are: cyclohexyl, phenyl, 4-fluorophenyl, 3-methyl-4-fluorophenyl, 2-chlorophenyl, 3-chlorophenyl, 4-chlorophenyl, 2-methylphenyl, 3-methylphenyl, 4-methylphenyl, 3-methyl-4-trifluoromethylphenyl.

Among the substituents $R^{12}$, those particularly preferred are: methyl, trifluoromethyl, isopropyl, isobutyl, cyclopentyl, cyclohexyl, phenyl, 4- fluorophenyl, 3-methyl-4-fluorophenyl, 2-chlorophenyl, 3-chlorophenyl, 4-trifluorophenyl.

(D) If Y-X-R denotes the group of the formula VI, the following meanings are preferred
X-Y the CH=CH or —CH$_2$—CH$_2$-group,
G-E the sequence of atoms as in (c) and (e)

Among the substituents R$^{13}$, those preferred are: H, methyl, ethyl, propyl, isopropyl, t-butyl, trifluoromethyl.

Among the substituents R$^{14}$, those preferred are: straight-chain C$_1$-C$_4$-alkyl, branched C$_3$-C$_6$-alkyl, trifluoromethyl and phenyl.

Among the substituents R$^{15}$, those preferred are: cycloalkyl having 5 or 6 ring carbon atoms, and phenyl which can in turn be substituted 1 or 2 times by methyl, ethyl, chlorine, bromine, fluorine or trifluoromethyl.

Among the substituents R$^{16}$, those preferred are: straight-chain C$_1$-C$_3$-alkyl, branched C$_3$-C$_6$-alkyl, trifluoromethyl, or phenyl which can in turn be substituted 1 or 2 times by methyl, ethyl, propyl, trifluoromethyl, chlorine or fluorine.

Among the substituents R$^{13}$, those mentioned hereinafter are particularly preferred: methyl, isopropyl, tertiary-butyl and trifluoromethyl.

Among the substituents R$^{14}$, those particularly preferred are: methyl, isopropyl, tertiary-butyl, trifluoromethyl and phenyl.

Among the substituents R$^{15}$, those particularly preferred are: cyclohexyl, phenyl, 2-methylphenyl, 3-methylphenyl, 4-methylphenyl, 4-fluorophenyl, 3-fluorophenyl, 2-fluorophenyl, 3-methyl-4-fluorophenyl, 2-methyl-4-fluorophenyl, 4-trifluoromethylphenyl, 3-trifluoromethylphenyl, 2-trifluoromethylphenyl, 3-trifluoromethyl-4-fluorophenyl, 2,4-dichlorophenyl, 2-methyl-4-chlorophenyl, 3-methyl-4-chlorophenyl.

Among the substituents R$^{16}$, those particularly preferred are: methyl, isopropyl, tertiary-butyl, trifluoromethyl, phenyl, 4-fluorophenyl, 4-trifluoromethylphenyl, 3-methyl-4-fluorophenyl and 2,4-dichlorophenyl.

The invention also relates to a process for the preparation of compounds of the general formula I or II, which comprises the fluoro synthon of the general formula VII

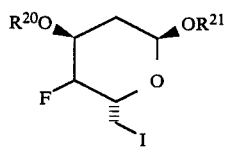

in which R$^{20}$ denotes a protective group which is stable to bases and weak acids, preferably benzyl, p-methoxybenzyl or t-butyldiphenylsilyl, R$^{21}$ denotes an acetal protective group which can be eliminated with weak acid, such as benzyl, methyl or ethyl, and the fluorine atom has either the R or the S configuration, (1)
(a) being reacted with phenols or thiophenols of the general formula

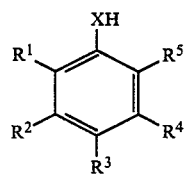

in which R$^1$ to R$^5$ have the meaning indicated for formula I, and X denotes oxygen or sulfur, to give the ethers of the formula IX

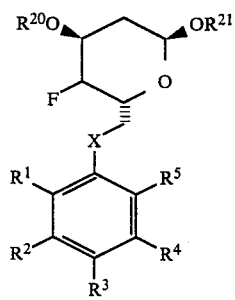

where R$^1$ to R$^5$ have the meanings indicated for formula I, R$^{20}$ and R$^{21}$ have the meanings indicated for formula VII, and X has the meanings indicated for formula VIII, (b) the ethers of the formula IX being hydrolyzed to give the corresponding hemiacetals of the formula

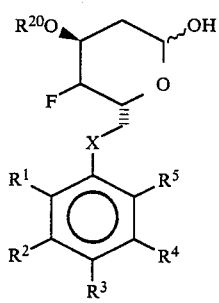

in which R$^1$ to R$^5$ have the meanings indicated for formula I, and R$^{20}$ has the meanings indicated for formula VII and X has the meanings indicated for formula VIII, (c) the hemiacetals of the formula X being oxidized to give the corresponding lactones of the formula XI

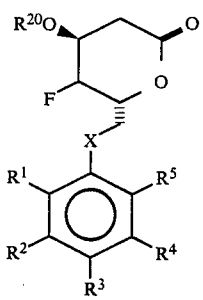

in which $R^1$ to $R^5$ have the meanings indicated for formula I, and $R^{20}$ has the meanings indicated for formula VII, and X has the meanings indicated for formula VIII, and (d) the protected hydroxy lactones of the formula XI being converted into the compounds of the formula I

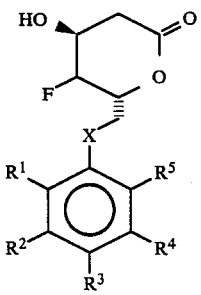

I (Y-X-R=group of the formula III) where appropriate the resulting compounds of the formula I being converted into the corresponding open-chain dihydroxy carboxylic acids of the formula II

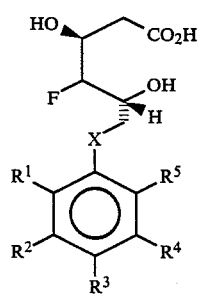

II or the salts thereof or the esters thereof, where appropriate resulting salts or esters being converted into the free dihydroxy carboxylic acids or, where appropriate, the free carboxylic acids being converted into the salts or esters, (2) (a) being reacted with triphenylphosphine to give the phosphonium salts of the formula XII

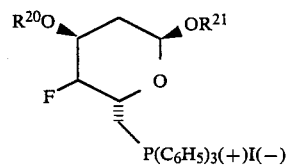

XII in which $R^{20}$ and $R^{21}$ have the meanings indicated for formula VII, (b) the phosphonium salts of the formula XII being converted in a Wittig reaction with aromatic aldehydes of the formula XIII

XIII in which R has the meanings indicated for formula I under B to D, into 4-fluoro-5-arylethene-substituted demethylmevalonic acid derivatives of the formula XIV

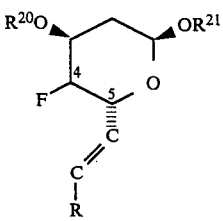

XIV in which R has the meanings indicated for formula I under B to D, and $R^{20}$ and $R^{21}$ have the meanings indicated for formula VII, (c) in a compound of the general formula XIV the $R^{21}$ acetal function being subjected to acid hydrolysis, and the $R^{20}$ protective group being either subjected to acid hydrolysis or removed by oxidation or eliminated by hydrogenolysis to give a lactol of the formula XV

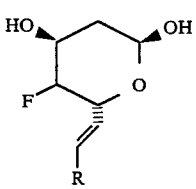

XV in which R has the meaning indicated for formula I under B to D, (d) the compound of the general formula XV being oxidized to give a lactone of the formula I

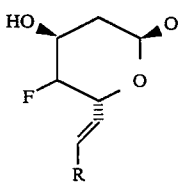

I in which R has the meanings indicated for formula I under B to D, (e) where appropriate a compound of the general formula I in which Y-X represents a (—CH=CH—) group being hydrogenated to give a compound of the general formula I in which Y-X represents a (—CH$_2$—CH$_2$—) group, it also being possible for the hydrogenation to take place with the compounds of the formulae XIV or XV to give corresponding compounds in which Y-X represents the (—CH$_2$—CH$_2$—) group, where appropriate a hydroxy lactone I being converted into the corresponding free hydroxy acids II or the salts thereof or, where appropriate, the corresponding ester being prepared from the free hydroxy acids II or from the hydroxy lactone I.

Process (1) is expediently carried out under the conditions described in the European patent application with the publication No. 0,216,127. Suitable reaction conditions, especially for the preparation of compounds in which X is sulfur, can also be found in German patent application P 36 32 893.6.

The aromatic aldehydes of the formula XIII carry as substituents R the groups which are listed for formula I under (B) to (D). Accordingly, they correspond to the following formulae:

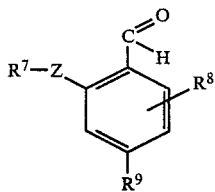
XIII a

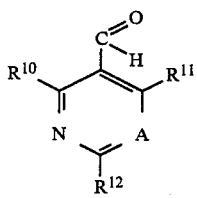
XIII b

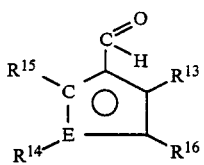
XIII c

The phosphonium salts XII in which $R^{20}$ and $R^{21}$ have the meaning indicated for formula VII are preferably prepared by fusing together the fluoro synthon VII and triphenylphosphine at elevated temperature, preferably 50°–110° C.

The procedure for the Wittig reaction for the preparation of the compound of the general formula XIV is, for example, that of Wittig and Haag, Chem. Ber. 88 (1955) 1654, with a preferred embodiment comprising the phosphonium salts of the formula XII being dissolved or suspended in a solvent such as tetrahydrofuran, dimethyl sulfoxide or dimethoxyethane at temperatures between −78° C. and −10° C., and the corresponding phosphoranes being liberated with a suitable strong base such as, for example, sodium hydride, potassium tertiary-butylate or butyllithium, and then the aldehyde of the formula XIII being added and allowed to react at −60° C. to +20° C. for 1 to 6 hours.

The demethylmevalonic acid derivatives of the formula XIV are usually obtained from this in the form of a mixture of the E/Z olefins which are, where appropriate, separated by chromatography. The pure Z olefins can be obtained, as described by G. Drefahl, Chem. Ber. 94 (1967) 907, by irradiation of the E/Z mixtures in solvents such as, for example, toluene or nitrobenzene; the corresponding pure E olefins can be obtained, as described by De Tar et al. in J. Am. Chem. Soc. 78 (1955) 474, by heating the E/Z mixtures in solution in the presence of iodine.

The compounds of the formula XIV are hydrolyzed, and the protective groups $R^{20}$ are eliminated, under customary conditions. The compounds of the formula XV are oxidized to give the lactones of the formula I likewise under conditions described in the literature.

Compounds of the formula I which are obtained and in which X-Y represents a (CH=CH) group can be hydrogenated by generally customary methods, expediently at temperatures between 20° and 40° C., with hydrogen in the presence of a metal catalyst, preferably palladium, platinum, $PtO_2$ or $PdO_2$, to give compounds of the formula I in which X-Y denotes a ($CH_2$—$CH_2$) group. This hydrogenation can be carried out under atmospheric pressure in customary solvents such as tetrahydrofuran, ethyl acetate, low molecular weight alcohols, glacial acetic acid, chloroform or cyclohexane, or in autoclaves under elevated pressure at 2–50 atm. The hydrogenation of the double bond can also take place on precursors.

The fluoro synthons of the formula VII are new and represent valuable intermediates for the preparation of compounds of the formula I.

Hence the invention also relates to the compounds of the formula VII as well as to the corresponding unprotected compounds of the formula VII ($R^{20}$ and $R^{21}$ equal to hydrogen) as well as to a process for the preparation of these compounds.

The process for the preparation of compounds of the general formula VII and the corresponding compounds without protective groups comprises
(a) the glycoside of the formula XVII

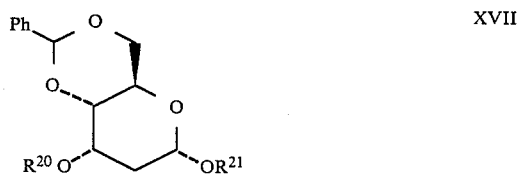
XVII in which $R^{20}$ and $R^{21}$ have the meanings indicated for formula VII, being converted into a compound of the formula XVIII

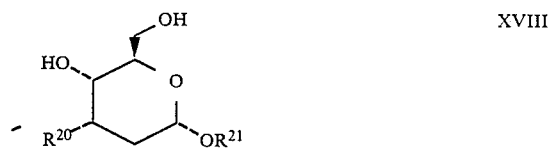
XVIII (b) the compound of the formula XVIII being acylated with an acylating agent to give a compound of the formula XIX

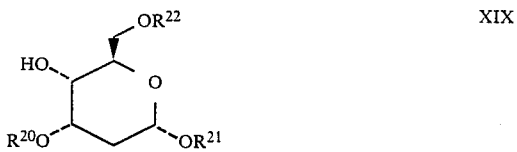
XIX in which $R^{20}$ and $R^{21}$ have the meanings indicated for formula VII, and $R^{22}$ is a

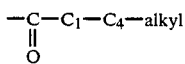

group or the benzoyl group, and
(c)

(1) either the acyl compound of the formula XIX being reacted with a fluorinating reagent to give a compound of the formula XXa

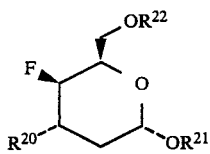

in which $R^{20}$, $R^{21}$ and $R^{22}$ have the indicated meanings, (2) or the acyl compound XIX being converted, by inversion of the configuration of the secondary alcohol function in a manner known per se in the presence of an acid carrying $R^{22}$, into a glycoside of the formula XXI

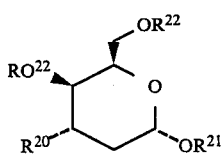

the acyl protective groups being removed from a compound of the formula XXI by alkaline hydrolysis, and regioselective acylation being carried out to give a compound of the formula XXII

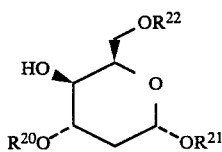

and the compound XXIII being converted by reaction with a fluorinating reagent into a compound of the formula XXb

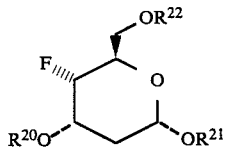

(d) the acyl group $R^{22}$ being eliminated by customary processes from a fluoro derivative of the formula XXa or b, and the primary alcohol function being converted by customary processes into a primary iodide of the formula VIIa or VIIb, for example by preparation of the corresponding p-toluenesulfonates and reaction thereof with sodium iodide, or by the Moffatt reaction, J. Org. Chem. 35 (1970), 2319, with methyltriphenoxyphosphonium iodide and, where appropriate, the groups $R^{20}$ and $R^{21}$ being removed by hydrolysis.

Glycosides of the formula XVII are either described in the literature or can be prepared in analogy to described methods (cf., for example, Prugh et al., J. Org. Chem. 51 (1986) 648). Thus, if the synthesis of the glycoside XVII starts from the α-methylglycoside of the formula XXIII, then the preparation of the fluoro synthon of the formula VII takes places as shown in the following reaction scheme (Scheme 1).

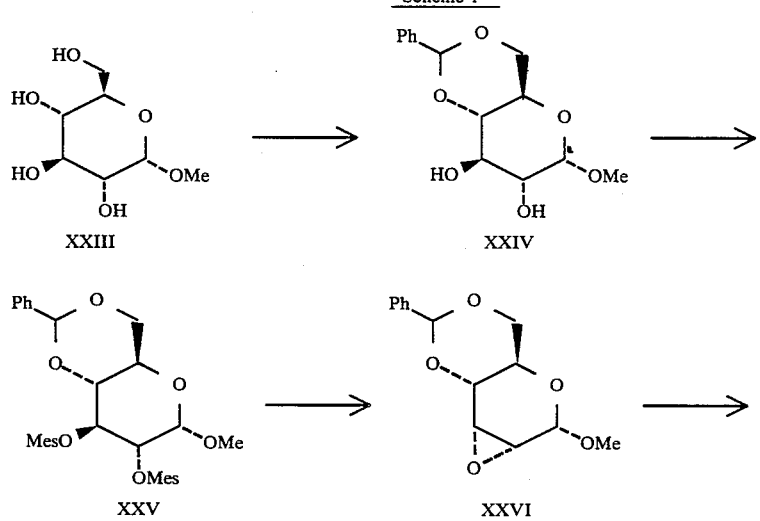

Scheme 1 -continued

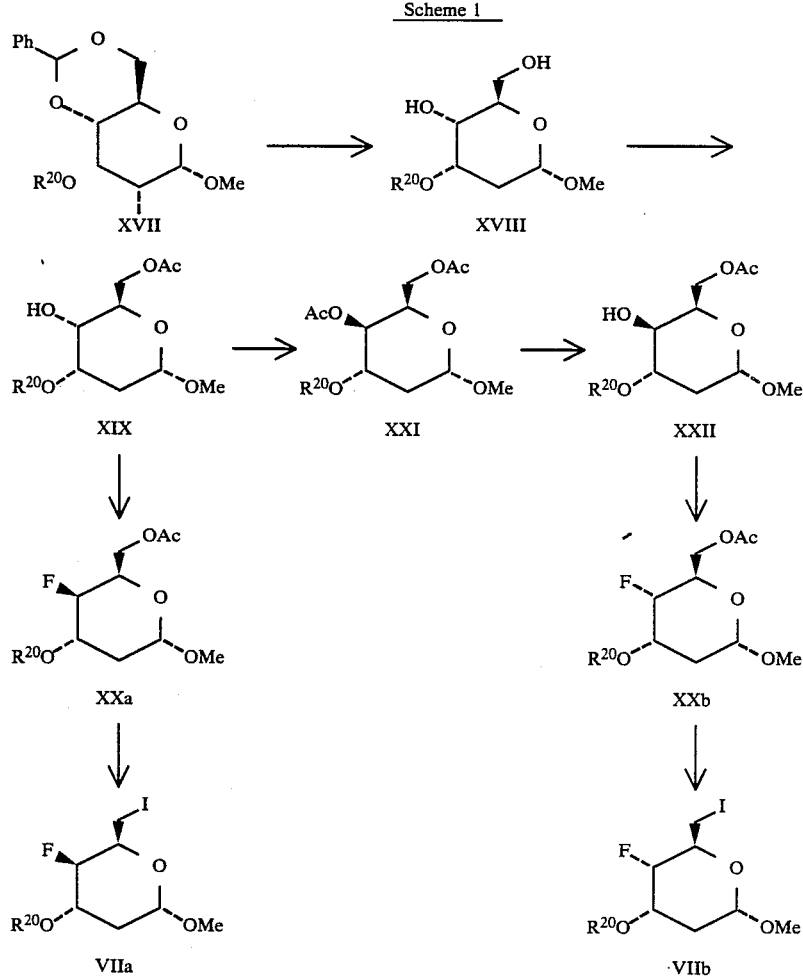

The preparation is expediently carried out as described hereinafter. The α-methylglycoside XXIII is reacted with benzaldehyde dimethyl acetal in an organic solvent, preferably DMF, with acid catalysis, for example para-toluenesulfonic acid or sulfuric acid, under reduced pressure and at elevated temperature (about 60° to 100° C.), to give the benzaldehyde acetal XXIV.

The latter is reacted with methanesulfonyl chloride in halogenated organic solvents, such as dichloromethane, with the addition of tertiary amines such as pyridine or triethylamine, to give the methanesulfonate of the formula XXV, and the latter is converted in a base-catalyzed transesterification followed by an intramolecular substitution into the epoxide of the formula XXVI (cf. N. K. Richtmeyer, C. S. Hudson, J. Am. Chem. Soc. 63, (1941), 1727), and this epoxide is converted by known processes (A. C. Richardson, Carbohydr. Res. 4 (1967), 422), into the corresponding 3-α-hydroxy-2-deoxysugar, in which the secondary alcohol is alkylated, for example with benzyl, methoxybenzyl or silyl halides, preferably with p-methoxybenzyl chloride or t-butyldiphenylsilyl chloride by customary methods (J. S. Brimacombe et al. J. Chem. Soc. Perkin I, 1977 643) to give the 2-deoxy-α-D-allopyranoside XVII. The glycoside of the formula XVII is converted, by removal of the benzyliodene protective group under acid conditions (Prugh et al., J. Org. Chem. 51 (1986) 5, 652), into the 2-deoxy-3-O-$R^{20}$-α-D-methylalloside of the formula XVIII, which is converted by regioselective acylation with acid chlorides or anhydrides, preferably acetic anhydride or pivaloyl chloride, in inert organic solvents such as diethyl ether, THF, methyl tertiarybutyl ether, DMF, toluene, dichloromethane or acetonitrile, with catalysis by a tertiary base, such as triethylamine or pyridine, into the 3-O-$R^{20}$-6-O-acyl-α-D-methylalloside of the formula XIX.

The latter is converted with a fluorinating reagent, such as sulfur tetrafluoride or dialkylaminosulfur trifluoride (see J. W. Middleton, J. Org. Chem. 40 (1975) 574, Merck-Schuchardt MS-Info 85-7), preferably diethylaminosulfur trifluoride (DAST), in an inert organic solvent such as dichloromethane, dichloroethane, 1,1,1-difluorochloro-2,2,2-fluorodichlorethane, tetrahydrofuran, toluene, diethyl ether or methyl tertiary-butyl ether, with the addition of an auxiliary base such as pyridine, triethylamine or diisopropylethylamine, at elevated temperature, preferably 80° C., into a (4R)-fluoro-substituted compound of the formula XXa, with inversion of the configuration of the original (4S)-hydroxyl group.

Inversion of the configuration of the secondary alcohol function in compound XIX by the method of Mitsunobu (Bull. Chem. Soc. Japan 44 (1971) 3427) with conversion into the 4-acetate of the formula XXI, or into the corresponding 4-formate or 4-benzoate, hydrolysis of the protective groups in the compound of the formula XXI by customary methods, preferably sodium methanolate in methanol, where appropriate protection of the 6-hydroxyl group by conversion into the corresponding acetyl or pivaloyl ester of the formula XXII, and fluorination of the (4R)-hydroxyl group as described above results in the (4S)-fluorinated compound of the formula XXb. From the fluoro derivatives of the formulae XXa and XXb there are obtained, after elimination of the 6-O-acyl protective groups by, for example, customary processes, the primary alcohol functions, and after conversion into the p-toluenesulfonates in halogenated solvents, preferably dichloromethane, with catalysis by a tertiary nitrogen base such as pyridine or triethylamine, and by reaction with inorganic iodide, preferably sodium iodide, in solvents such as acetone or DMF, at temperatures between 50° and 110° C., the iodo lactols of the formula VII. The latter can, where appropriate, be purified by chromatography or converted directly by reaction with triphenylphosphine, for example in the melt at elevated temperatures, preferably 80°–110° C., into the phosphonium salts of the formula XII.

PREPARATION OF THE STARTING COMPOUNDS

The phenols of the general formula VIII with X=oxygen, which are used as starting material, are either described in the literature or can be prepared in analogy to described processes (cf., for example, European patent application with the publication No. 0,216,127).

The thiophenols of the formula VIII with X=sulfur are likewise either described in the literature or can be prepared in analogy to described processes (cf., for example, J. Org. Chem. 31, 3980 (1966) and German patent application Ser. No. P 36 32 893.6).

The preparation of the substituted aromatic aldehydes of the formula XIIIa starts from the corresponding benzyl halides of the formula XXVII

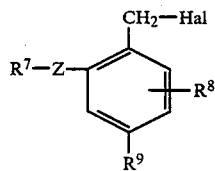

XXVII in which $R^7$ to $R^9$ and Z have the meaning indicated for formula I, and Hal is chlorine, bromine or iodine. One process for the preparation of benzyl halides of the formula XXVII is described in European patent application with the publication No. 0,217,092. The halides of the formula XXVII are oxidized to the corresponding benzaldehydes of the formula XIIIa using DMSO in the presence of silver(I) ions and triethylamine as described by B. Ganem, R. K. Boeckman, Tetrahedron Lett. 1974, 917. The synthesis can also be carried out by the method of S. Murahashi, as described, for example, by G. E. Stokker et al., J. Med. Chem. 29 (1986) 173.

One process for the preparation of pyridine-3-carbaldehydes and pyrimidine-5-carbaldehydes of the general formula XIIIb starts from the corresponding hetarylmethyl alcohol of the formula XXVIII

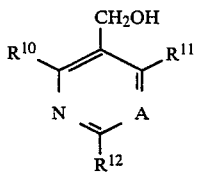

XXVIII in which $R^{10}$ to $R^{12}$ and A have the meaning indicated for formula V. These alcohols can be obtained from the corresponding esters by reduction with customary reducing agents, preferably Li aluminum hydride. These pyrimidine or pyridinecarboxylic esters can be obtained by processes known from the literature [Pyridines by the method of F. Rehberg and F. Kröhnke, Liebigs. Ann. Chem. 717 (1968) 19; Pyrimidines: E. F. Silversmith, J. Org. Chem. 27 (1962) 4090]. One process for the preparation of the alcohols of the formula XXVIII is, furthermore, proposed in German patent application Ser. No. P 37 22 808.0 of July 10, 1987.

The aldehydes of the formula XIIIb are obtained by oxidation of the alcohols by customary methods, preferably pyridinium chlorochromate in inert organic solvents, preferably dichloromethane, under the catalytic action of molecular sieves, by the method of J. Herscovici and K. Antonakis (J. Chem. Soc. Chem. Comm. 1980, 561).

Heterocyclic aromatic aldehydes of the general formula XIIIc are prepared, for example, by reduction of the corresponding carboxylic esters by customary processes to give the alcohol XXIX

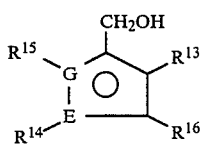

XXIX in which $R^{13}$ to $R^{16}$ have the meanings indicated for formula I, followed by oxidation thereof to give the aldehyde XIIIc by customary processes such as, for example, in A. J. Mancuso et al., J. Org. Chem. 43 (1978) 2480; the preparation of the caroboxylic esters is described in the literature.

(a) for example for G-E equal to S—C: J. M. Spragur et al., J. Am. Chem. Soc. 56 (1934) 2665; Heterocyclic Compounds Vol. 44, Part 1, Thiophene and Derivatives, J. Wiley & Sons, N.Y. 1985, especially page 197;

(b) G-E equal to C—S: S. Gronowitz et al., Acta pharm. sued. 9 (1972) 301;

(c) G-E equal to C—O: F. Boberg et al., Liebigs Ann. Chem. 1984, 233;

(d) G-E equal to C—N: European patent application Ser. No. 0,221,025-A 1 or is effected by analogous methods. The preparation of aldehydes of this type is likewise proposed in German patent application Ser No. P 37 22 806.4 of July 10, 1987, and in European patent application Ser. No. 0,221,025 A1.

Apart from the compounds described in the examples, it is possible by the process according to the invention to prepare the following compounds:

E-6R-[2-(2-(4-Fluoro-3-methylphenyl)-4,6-dimethylphenyl)-ethenyl]-5(R)-fluoro-4(S)-hydroxy-3,4,5,6-tetrahydro-2H-pyran-2-one E-6R-[2-(3-(4-Fluorophenyl)-1-isopropyl)-1H-indol-2-yl)ethenyl]-5(R)-fluoro-4(S)-hydroxy-3,4,5,6-tetrahydro-2H-pyran-2-one E-6R-[2-(1-Phenyl-2-isopropyl-4-(4-fluorophenyl)1H-pyrrol-b 3-yl)ethenyl]-5(R)-fluoro-4(S)-hydroxy-3,4,5,6-tetrahydro-2H-pyran-2-one E-6R-[2-(2-(4-Fluorophenyl)-4-phenyl-6-isopropylphenyl)-ethenyl] -5(R)-fluoro-4(S)-hydroxy-3,4,5,6-tetrahydro-2H-pyran-2-one E-6R-[2-(2-(4-Fluorophenyl-4-phenyl-6-isopropylphenyl)-ethyl]-5(R)-fluoro-4(S)-hydroxy-3,4,5,6-tetrahydro-2H-pyran-2-one 6R-[1-(2-(4-Fluorophenyl)-4-phenyl-6-isopropylphenoxy)-methyl]-5(R)-fluoro-4(S)-hydroxy-3,4,5,6-tetrahydro-2H-pyran-2-one 6S-[1-(2-(4-Fluorophenyl)-4-phenyl-6-isopropylphenylthio)-methyl]-5(R)-fluoro-4(S)-hydroxy-3,4,5,6-tetrahydro-2H-pyran-2-one E-6R-[2-(4-(4-Fluorophenyl)-2-isopropyl-6-phenylpyridin-3-yl)ethenyl]-5(R)-fluoro-4(S)-hydroxy-3,4,5,6-tetrahydro-2H-pyran-2-one E-6R-[2-(4-(4-Fluorophenyl)-2-isopropyl-6-phenylpyridin-3-yl)ethyl]-5(R)-fluoro-4(S)-hydroxy-3,4,5,6-tetrahydro-2H-pyran-2-one E-6R-[2-(4-(4-Fluorophenyl)-6-isopropyl-2-phenylpyrimidin-5-yl)ethenyl]-5(R)-fluoro-4(S)-hydroxy-3,4,5,6-tetrahydro-2H-pyran-2-one E-6R-]2-(4-(4-Fluorophenyl)-6-isopropyl-2-phenylpyrimidin-5-yl)ethyl]-5(R)-fluoro-4(S)-hydroxy-3,4,5,6-tetrahydro-2H-pyran-2-one E-6R-[2-(2,5-di-tertiary-butyl-4-phenyl-3-thienyl)-ethenyl]-5(R)-fluoro-4(S)-hydroxy-3,4,5,6-tetrahydro-2H-pyran-2-one (The numbering is in accordance with the pyran nomenclature)

The inhibition of HMG-CoA reductase activity by the compounds of the general formulae I and II was determined on solubilized enzyme preparations from rat liver microsomes.

After changeover of the day/night rhythm of the rat, enzyme formation was induced with cholestyramine (® Cuemid). The substrate used was (S,R)-$^{14}$C-HMG-CoA, and the concentration of NADPH was maintained during the incubation by a regenerating system. $^{14}$C-mevalonate was removed from the substrate and other products (for example $^{14}$C-HMG) by column elution, with the elution profile of each individual sample being determined. $^3$H-mevalonate was not always included in the determination because relative data on the inhibitory effects were required. In each series of tests, the enzyme-free control, the enzyme-containing normal mixture (=100%) and those with additions of product were treated together. Each individual value was the mean formed from 3 parallel samples. The significance of the mean differences between product-free and product-containing samples was assessed using the t test.

Using the method described above, the values given in Table I for the inhibition of HMG-CoA reductase were determined for the compounds according to the invention (IC$_{50}$ value M=molar concentration of the compound necessary for 50% inhibition. In each case the IC$_{50}$ values for the optically pure compounds I in the preferred absolute configuration are given).

TABLE I

| Compound of Example | IC$_{50}$ value M |
|---|---|
| 12 | $2 \times 10^{-6}$ |
| 18 | $3.2 \times 10^{-8}$ |
| 35 | $8.5 \times 10^{-9}$ |
| 41 | $2.0 \times 10^{-8}$ |
| 42 | $3.6 \times 10^{-8}$ |
| 43 | $6.3 \times 10^{-9}$ |
| 44 | $9.8 \times 10^{-8}$ |

In addition, the inhibition of cholesterol biosynthesis in cell cultures was tested with selected compounds by the incorporation of $^{14}$C-precursor in cholesterol.

Monolayers of HEP G2 cells in Lipoprotein-free nutrient medium were incubated with various concentrations of the test substances for 1 hour. After addition of the $^{14}$C-labeled precursor sodium $^{14}$C-acetate, the incubation was continued for 3 hours. Then $^3$H-cholesterol was added as internal standard, and some of the cells were hydrolyzed with alkali. The lipids were extracted from the hydrolyzed cells using chloroform/methanol. Carrier cholesterol was added to this lipid mixture which was then subjected to preparative thin-layer chromatography, the cholesterol band was visualized with iodine vapor and then isolated, and the amount of $^{14}$C-cholesterol formed from the $^{14}$C-precursor was determined by scintigraphy. Cellular protein was determined in an aliquot of the cells, so that it is possible to calculate the amount of $^{14}$C-cholesterol formed from the $^{14}$C-precursor per mg of cellular protein in unit time. The solvent control is used for comparison with the inhibitory effect of an added test product, so that the inhibition of cholesterol biosynthesis at a particular molar concentration of the test product in the medium can be stated. The absence of cell damage due to the action of the products was confirmed in an aliquot of the cell culture by the morphology (light microscope). The IC$_{50}$ values of the test products are stated in mol/l (in Table II), and their relative potencies are compared with mevinolin sodium salt and mevinolin lactone (comparison of the IC$_{50}$ values).

TABLE II

| Compound of Example | IC$_{50}$ value for inhibition of biosynthesis [mol/l] |
|---|---|
| 12 | $5.5 \times 10^{-6}$ |
| 18 | $3.2 \times 10^{-7}$ |
| 38 | $2.5 \times 10^{-7}$ |
| 34 | $1.1 \times 10^{-7}$ |

The compounds of the general formulae I and II are distinguished by potent inhibition of HMG-CoA reductase, the rate-determining enzyme of cholesterol biosynthesis. The enzyme HMG-CoA reductase is widespread in nature. It catalyzes the formation of mevalonic acid from HMG-CoA.

This reaction is a central step in cholesterol biosynthesis (cf. J. R. Sabine in CRC Series in Enzyme Biology: 3-Hydroxy-3-methylglutaryl Coenzyme A Reductase, CRC Press Inc. Boca Raten, Florida 1983 (ISBN 0-8493-6551-1)).

A connection is drawn between high cholesterol levels and a number of disorders such as, for example, coronary heart disease or arteriosclerosis. Hence the lowering of elevated cholesterol levels is an aim of therapy for the prevention and treatment of disorders of these types.

One approach to this is the inhibition or reduction of endogenous cholesterol biosynthesis. Inhibitors of HMG-CoA reductase block cholesterol biosynthesis at an early stage.

The cholesterol-lowering efficacy was investigated in the following test on rabbits Normolipidemic male New Zealand rabbits (weight 3–3.5 kg, 4–6 animals per test group) received the test compounds suspended in a 1% strength aqueous carboxymethylcellulose solution (®Tylose) by gavage each day in the morning; the control group received only Tylose solution. Venous blood was taken every 3 to 4 days 20 hours after the oral administration of the solutions. The total cholesterol content in these samples was determined enzymatically using the Boehringer Mannheim assay kit (CHOD-PAP-high performance method). The serum cholesterol level in the group treated with test compounds was compared with that in the control group. The treatment period was followed by a period in which the test compounds were no longer administered.

In this test, administration of the compound from Example 34 (10 mg/kg/day) resulted in a 40% lowering of total cholesterol within 3 days, and this remained constant throughout the administration without eliciting abnormal or pathological changes in the liver enzyme levels. The serum cholesterol levels returned to their initial value within 3 days after discontinuation of the product (after 10 days).

Hence the compounds of the general formulae I and II are suitable as hypolipidemics and for the treatment or prophylaxis of arteriosclerotic changes.

Hence the invention also relates to pharmaceutical products based on these compounds, and to the use thereof as medicaments, especially as hypolipidemics and for the prophylaxis of arterioslerotic changes.

The compounds of the formulae I and II are used as hypolipidemics or anti-arteriosclerotics in oral doses of 3 to 2500 mg, but preferably in the dose range 10–500 mg. These daily doses can, wherever required, also be divided into two to four single doses or be administered in sustained release form. The dosage regimen may depend on the type, age, weight, sex and medical condition of the patient.

An additional cholesterol-lowering effect can be achieved by concurrent administration of the compounds according to the invention with substances which bind bile acids, such as, for example, anion exchanger resins. The increase excretion of bile acids results in an enhanced neosynthesis and thus in an increase in cholesterol breakdown (cf. M. S. Brown, P. T. Koranen and J. C. Goldstein, Science 212, 628 (1981); M. S. Brown, J. C. Goldstein, Spektrum der Wissenschaft 1985, 1, 96).

The compounds according to the invention can be used in the form of the δ-lactones, as the free acids or in the form of their physiologically acceptable inorganic or organic salts or as esters. Acids and salts or esters can be used in the form of their aqueous solutions or suspensions, or else dissolved or suspended in pharmacologically acceptable organic solvents such as monohydric or polyhydric alcohols such as, for example, ethanol, ethylene glycol or glycerol, in triacetin, in alcohol/acetaldehyde diacetal mixtures, oils, such as, for example, sunflower oil or fish liver oil, ethers such as, for example, diethylene glycol ether or polyethers such as, for example, polyethylene glycol, or in the presence of other pharmacologically acceptable polymeric vehicles such as, for example, polyvinylpyrrolidone, or in solid formulations.

The preferred pharmaceutical forms for the compounds of the formulae I and II are solid, can be administered orally and may contain the customary auxiliaries. They are produced by customary methods.

Particularly suitable formulations for oral use are tablets, coated tablets or capsules. One dosage unit preferably contains 10 to 500 mg of active ingredient.

EXAMPLE 1

4,6-O-Benzylidene-α-D-methylglucoside (Scheme 1, formula XXIV)

2.3 mol (446 g) of α-methylglucoside (Scheme 1, formula XXIII) were dissolved in 4.6 l of dry DMF, 3.0 mol (455 g) of benzaldehyde dimethyl acetal and 0.023 mol (4.4 g) of p-toluenesulfonic acid monohydrate were added, and the mixture was maintained at 90° C. and 40 mm Hg, with exclusion of moisture and methanol being distilled out by means of a distillation apparatus, for 12 hours.

After cooling and addition of 60 g of NaHCO$_3$, the mixture was vigorously stirred for 1 h, the precipitate was filtered off with suction, the solvent was removed by distillation, the residue was taken up in dichloromethane, and the solution was washed with saturated NaHCO$_3$ solution. The organic phase was washed with saturated Na$_2$SO$_4$ and filtered. The filtrate was concentrated and then the residue was triturated with petroleum ether, filtered off with suction and washed copiously with petroleum ether.

519 g (1.84 mol) (corresponding to an 80% yield) of white solid were obtained, melting point 162°–163° C. (EtOH).

EXAMPLE 2

2,3-Di-O-mesyl-4,6-O-benzylidene-α-D-methylglucoside (Scheme 1, formula XXV)

1 mol (282 g) of the compound from Example 1 was dissolved in 2.5 l of methylene chloride, and 2.5 mol (253 g) of triethylamine and 0.14 mol (17 g) of 4-dimethylaminopyridine were added. 2.5 mol (286 g) of mesyl chloride were added dropwise to this solution at 0° C., with exclusion of moisture, and the mixture was stirred at this temperature for 2 h and then at room temperature for 2 days. The organic phase was then washed 2× with 1.25 l of water, dried over $Na_2SO_4$ and concentrated. The residue was triturated with methanol, filtered off with suction and dried. 390 g (0.89 mol)=89% of white solid were obtained, melting point 189°–190° C. (MeOH).

$^1$H-NMR (200 MHz, $CDCl_3$): $\delta=3.0$ (s; 3H, $SO_2CH_3$), 3.2 (s; 3H, $SO_2CH_3$), 3.5 (s; 3H, $OCH_3$), 3.7–4.0 (m; ABM System; 3H, 6-$H_2$ and 5-H); 4.33 (dd, J=4.0 Hz, J=9,0 Hz; 1H, 4-H); 4.65 (dd, J=4.0 Hz, J=9,0 Hz; 1H, 3-H); 4.9–5.2 (m; 2H, 2-H and 1-H), 5.56 (s; 1H, O—CH—O); 7.3–7.5 (m; 5-H, Aryl-H).

EXAMPLE 3

2,3-Anhydro-4,6-O-benzylidene-α-methyl-D-alloside (Scheme 1, formula XXVI)

1 mol (439 g) of the compound from Example 2 was dissolved in 6.5 l of methylene chloride, 8 mol (432 g) of sodium methanolate were added, and the mixture was refluxed until reaction was complete, about 3 h (TLC: cyclohexane:ethyl acetate:toluene=1:2:1, $R_f$(XXVI)=0.47). The solution was then washed with water, dried over $Na_2SO_4$ and concentrated. The residue was triturated with ether, and the precipitate was filtered off with suction and dried (80° C., 1 mm Hg). 209 g (0.79 mol)=79% of a white solid were obtained, melting point 201°–202° (acetone).

$^1$H-NMR (60 MHz, $CDCl_3$): $\delta=3.5$ (s; 3H, $OCH_3$), 3.4–4.5(m; 6H, 2-H, 3-H, 4-H, 5-H, 6-$H_2$), 4.8 (d, J=2.0 Hz; 1H, 1-H); 5.6 (s; 1H, Benzylidene-H); 7.2–7.6 (m; 5H, Aryl-H).

EXAMPLE 4

3-O-Benzyl-4,6-O-benzylidene-2-deoxy-α-methyl-D-allopyranoside (Scheme 1, Formula XVII)

The compound was prepared by known processes in two stages from the compound from Example 3. Lithium alanate reduction, by the method of A. C. Richardson, Carbohydr. Res. 4, (1967) 422, of 1 mol (264 g) of the compound from Example 3 yields 224 g (0.84 mol)=84% of 4,6-O-benzylidene-2-deoxy-α-methyl-D-allopyranoside of melting point 130°–131° C. (EtOH/petroleum ether=1:4). Alkylation of this compound by the method of Brimacombe (J. S. Brimacombe et al. J. Chem. Comm. Perkin I, 1977, 643) with benzyl bromide in dimethylformamide yielded 207 g (0.58 mol)=69% of the compound of the formula XVII, melting point 98°–100° C. (cyclohexane); $[\alpha]_D=+63°$ (C=0.7, $CHCl_3$). $^1$H-NMR (200 MHz, $[D]_6$-DMSO): $\delta=1.9$ (ddd, J=15 Hz, J=4 Hz, J=6 Hz; 1H, 2-$H_{ax}$), 2.15 (dd, J=15 Hz, J=3 Hz; 1H, 2-$H_{eq}$); 3.3 (s; 3H, $OCH_3$); 3.6–3.8 (m; 2H, 6-H, 5-H); 3.9 (ddd, J=3 Hz, J=3 Hz, J=4 Hz; 1H, 3-H); 4.1–4.3 (m; 2H, 6-H, 4-H); 4.6 AB-System; 2H, Benzyl-$H_2$); 4.7 (d, J=5 Hz; 1H, 1-H); 5.7 (s; 1H, Benzylidene-H); 7.2–7.5 (m; 10H, Aryl-H).

ms (70 eV): m/e=356 ($M^+$), 324 ($M^+$—$CH_3OH$), 91 (Benzyl). TLC (cyclohexane:ethyl acetate=1:1, silica gel 60 $F_{254}$/0.25 mm, Riedel de Haen): $R_f$(XXVI)=0.28, $R_f$(XVII)=0.46.

EXAMPLE 5

6-O-Acetyl-3-O-benzyl-2-deoxy-α-methyl-D-allopyranoside (Scheme 1, formula XIX)

(a) 0.1 mol (35.6 g) of the compound from Example 4 was dissolved in 70 ml of dichloromethane, 3 ml of 70% strength aqueous trifluoroacetic acid were added, and the mixture was vigorously stirred for 1 hour. TLC (cyclohexane/ethyl acetate—1:1): $R_f$(XVII)=0.46, $R_f$(3-O-benzyl-α-methyl-D-allopyranoside)=0.08. 20 ml of saturated sodium bicarbonate solution were added, and the mixture was stirred vigorously for 10 min. The phases were separated and then the organic phase was dried and concentrated, and the benzaldehyde produced was removed by distillation under high vacuum. 23 g (0.08 mol)=84% of a colorless oil were obtained.

(b) The resulting product was dissolved in 320 ml of dichloromethane, 2.5 equivalents of pyridine were added, and the mixture was cooled to 0° C. 0.088 mol (9 g) of acetic anhydride was added dropwise, and the mixture was stirred at room temperature for 12 h. It was then washed with saturated $NaHCO_3$ solution and water, dried and concentrated. Purification was by column chromatography on silica gel, cyclohexane/ethyl acetate 1:1. 16 g (0.054 mol)=67% of XIX were obtained as a colorless oil, $R_f$ (cyclohexane/ethyl acetate 1:1)=0.28.

$^1$H-NMR (270 MHz, $CDCl_3$): $\delta=1.78$ (ddd, $J_{2,2}=15.0$, $J_{2,1}=4,5$, $J_{2,3}=3,5$ Hz; 1H, 2- Hax; 2.10 (s; 3H, $COCH_3$); 2.35 (ddd, J=15.0 Hz, $J_{2,3}=3.0$ Hz, $J_{2,1}=1.0$ Hz; 1H, 2-Heq); 2.65 (d, J=10 Hz; 1H, OH); 3.37 (s; 3H, $OCH_3$); 3.58 )dt, $J_{5,6}=10.0$ Hz, $J_{5,4}=4.2$ Hz; 1H, 5-H); 3.89 (ddd, $J_{3,2}=3.0=J_{3,4}=3.0$, $J_{3,2ax}=3.5$ Hz; 1H, 3-H); 4.08 (ddd, $J_{4,4}=10.0$, $J_{4,5}=4.2$, $J_{4,3}=3.0$ Hz; 4-H); 4.34 (m, AB-part; 2H, 6-H); 4.39 and 4.82 (AB-System; 2H, Benzyl-$CH_2$); 4.75 (d, J=4.5 Hz; 1H, 1-H), 7.30–7.45 (m; 5H, Aryl-H).

EXAMPLE 6

6-O-Acetyl-3-O-benzyl-4-O-deoxy-4-fluoro-α-methyl-D-gulopyranoside (Scheme 1, formula XXa)

16 g (0.052 mol) of the compound from Example 5 and 0.15 mol (19 g) of ethyldiisopropylamine were introduced under nitrogen into 500 ml of absolute toluene. While stirring at −10° C. under $N_2$, 0.10 mol (16.76 g) of diethylaminosulfur trifluoride (DAST, Merck-Schuchardt) was added dropwise in such a way that the temperature remained below 0° C. The mixture was then stirred at this temperature for 30 min, allowed to reach room temperature and heated at 80° C. for 2 h. Ice-cold saturated $NaHCO_3$ solution was added to the vigorously stirred solution at room temperature until no more gas evolution was detectable. The phases were then separated, the aqueous phase was extracted with methylene chloride, and the organic phases were dried and concentrated in a rotary evaporator. Purification was by preparative column chromatography on silica gel (®AMICON 35–70 μ, 60 Å; cyclohexane:ethyl acetate=1:1). 9.6 g (0.031 mol)=59% of a pale yellow oil were obtained.

$^1$H-NMR (270 MHz, $CDCl_3$): $\delta=1.95$ (ddd, $J_{2,2}=14.0$, $J_{2,3}=3.5$, $J_{2,1}=2.0$ Hz; 2H, 2-$H_{ax}$); 2.08

(dddd, $J_{2,2}$=14.0, $J_{2,3}$=4.0, $J_{2,1}$=4.5, $J_{2,4}$=2.5 Hz; 1H, 2H$_{eq}$); 2.10 (s; 3H, COCH$_3$); 3.42 (s; 3H, OCH$_3$); 3.81 (dddd, $J_{3,F}$=8.0, $J_{3,2}$=$J_{3,2}$=$J_{3,4}$=4.0 Hz; 1H, 3-H); 4.15-4.35 (m; 3H, 6-H$_2$, 5-H); 4.50 (dd, $J_{4,F}$=48.0, $J_{4,3}$=4.0 Hz; 1H, 4-H); 4.65 (m$_c$, AB-System; 2H, Benzyl-H); 4.80 (dd, $J_{1,2}$=2.0, $J_{1,2}$=4.5 Hz; 1H, 1-H); 7.25-7.45 (m; 5H, Benzyl-H). ms (70 eV); m/e=311 (M$^+$—H), 281 (M$^+$—OCH$_3$), 220, 145, 91, 43.

TLC (silica gel 60, cyclohexane/ethyl acetate=1:1): R$_f$(XIX)=0.28, R$_f$(XXa)=0.53.

EXAMPLE 7

3-O-Tertiary-butyldiphenylsilyl-2,4-dideoxy-4(R)-fluoro-6-deoxy-6-iodo-α-methyl-D-gulopyranoside (formula VII with R$^{21}$=CH$_3$ and R$^{20}$=t-BuPh$_2$Si)

(a) 6-O-Acetyl-4-deoxy-4-fluoro-α-methyl-D-gulopyranoside 19.5 g (0.062 mol) of the compound from Example 6 in 30 ml of methanol were mixed with prehydrogenated catalyst, 10% Pd/charcoal, 2.0 g, and hydrogenated under atmospheric pressure in a shaken vessel until 1.4 l of H$_2$ had been absorbed; TLC (cyclohexane:ethyl acetate=1:1): R$_f$(XXa)=0.51, R$_f$(product)=0.27. The catalyst was removed by filtration, and the filtrate was concentrated. 12.9 g (0.058 mol)=93% of a colorless oil were obtained.

$^1$H-NMR (270 MHz, CDCl$_3$): δ=1.9 (d, J=14 Hz; 1H, 2-H$_{ax}$), 2.10 (s; 3H, OAc); 2.18 (dddd, J=15 Hz; J=J=J=4.0 Hz; 1H, 2-H$_{eq}$); 3.40 (s; 3H, OCH$_3$); 3.60 (d, J=10 Hz; 1H, OH); 4.04 (m (br); 1H, 3-H); 4.13-4.38 (m; 3H, 5-H, 6-H$_2$); 4.49 (dd, J=48 Hz, J=4 Hz; 1H, 4-H); 4.90 (d, J=4 Hz; 1H, 1-H).

(b) 6-O-Acetyl-3-O-tertiary-butyldiphenylsilyl-2,4-dideoxy-4-fluoro-α-methyl-D-gulopyranoside 21 mmol (4.9 g) of the alcohol from stage a which had been dried over CaCl$_2$ were dissolved in 50 ml of absolute DMF, 11 ml of triethylamine were added and, under nitrogen, 1 g (8 mmol) of 4-DMAP was added, and the mixture was stirred at RT. To this were added dropwise 1.5 equivalents (0.032 mol, 8.43 ml) of tertiary-butyldiphenylchlorosilane. The mixture was left to stir at room temperature for 15 hours and then heated at 90° C. for 6 h. It was then evaporated to dryness, the residue was taken up in 100 ml of CH$_2$Cl$_2$, and a solution was extracted twice with 100 ml of saturated NaHCO$_3$ solution. The phrases were separated, and the organic phase was dried over Na$_2$SO$_4$ and concentrated. Purification by chromatography on 200 g of silica gel 60, cyclohexane:ethyl acetate (6:1): elution of 200-800 ml. 9.5 g (21 mmol)=100% of a pale yellow oil were obtained.

TLC (cyclohexane/ethyl acetate=6:1): R$_f$(precursor from stage a)=0.11 R$_f$(product from stage b)=0.49, R$_f$(t-BuPh$_2$SiCl)=0.74. [α]$_D$=+38.5° (c=1, CHCl$_3$).

$^1$H-NMR (400 MHz, CDCl$_3$): δ=1.10 (s; 9H, C(CH$_3$)$_3$), 1.71 (ddd, J=14.6, J$_{2,3}$=4.0, J$_{2,1}$=2.0 Hz; 1H, 2-H$_{ax}$), 1.87 (dddd, J=14.6, J$_{2,1}$=4.5, J$_{2,3}$=4.0 J$_{2,7}$=1.5 Hz; 1H, 2-H$_{eq}$), 2.09 (s; 3H, OAc), 3.40 (s; 3H, OCH$_3$), 4.09 (dddd, J=8.0, J=4.0, J=4.0, J=5.0 Hz; 1H, 3-H), 4.19 (dd, J$_{6,6}$=11.5, J$_{6,6}$=5.5 Hz; 1H, 6-H$_a$), 4.28 (dd, J$_{6,6}$=11.5, J$_{6,5}$=7.0 Hz; 1H, 6-H$_b$), 4.32 (ddd, J$_{4,F}$=48.0, J$_{4,3}$=5.0 Hz, J$_{4,5}$ 1.0 Hz; 1H, 4-H), 4.41 (ddd, J$_{5,F}$=31.0, J$_{5,6}$=7.0, J$_{5,6}$=5.5 Hz; 1H, 5-H), 4.7 (dd, J$_{1,2}$=2.0 Hz, J$_{1,2}$=4.5 Hz; 1H, 1-H), 7.30-7.50 (m; 5H, Aryl-H), 7.60-7.80 (m; Aryl-H).

$^{13}$C-NMR (100 MHz, COCl$_3$): δ=19.14 (s; C(CH$_3$)$_3$, 20.7 (q, COCH$_3$), 26.7 (q, C(CH$_3$)$_3$), 31.6 (dd, C-2), 54.9 (q, CH$_3$), 63.1 (t, d, J$_{6,H}$=131 Hz, J$_{6,F}$=6.5 Hz; C-6); 63.6 (dd, J$_{5,H}$=146 Hz, J$_{5,F}$=17.6 Hz; C-5); 65.6 (dd, J$_{3,H}$=156 Hz, J$_{3,F}$=28.9 Hz; C-3); 87.8 (dd, J$_{4,H}$=156 Hz, J$_{4,F}$=182.3 Hz; C-4); 97.7 (d, J$_{C,H}$=166 Hz; C-1); 133.3, 133.4 (s; C-1'), 127.6, 127.7 (d, C-3'), 129.8, 129.9 (d, C-4'), 135.6, 135.8 (d, C-2'), 170.60 (s, C=0).

$^{19}$F-NMR (94.2 MHz, CDCl$_3$): δ=204.87;

ms (70 eV/150°): m/e=461 (M$^+$), 403 (M$^+$—C$_4$H$_9$), 371 (403—CH$_3$OH), 343 (403—CH$_3$COOH), 213 ((Ph)$_2$SiOCH$_3$), 199 ((Ph)$_2$SiOH), 177, 135, 43.

(c) 3-O-Tertiary-butyldiphenylsilyl-2,4-dideoxy-4-fluoro-6-deoxy-6-iodo-α-methyl-D-gulopyranoside (α) 17.4 mmol (8.0 g) of the acetate from stage b were dissolved in 17.4 ml of methanol, cooled to 0°, and 0.35 ml of a 1 M solution of NaOMe in MeOH was added. The solution was stirred at this temperature for 6 hours and was filtered through 10 g of acidic ion exchanger (for example ®Amberlyst 15), which had previously been swollen with methanol, and was then washed with methanol, and was evaporated to dryness.

6.8 g (16.3 mmol)=94% of a colorless oil were obtained.

TLC (cyclohexane:ethyl acetate=6:1): R$_f$(precursor from stage b)=0.52, R$_f$(product from stage α)=0.25.

(β) The oil was dissolved in 40 ml of pyridine/dichloromethane (1:1), 24 mmol (4.6 g) of p-toluenesulfonyl chloride were added, and the mixture was stirred with exclusion of moisture for 2 days. It was then concentrated, the residue was taken up in ether, and the solution was filtered and concentrated. The resulting crude product (8.7 g) was reacted further without purification.

(γ) It was dissolved in 120 ml of absolute DMF, 36 g (0.24 mol) of sodium iodide were added, and the components were stirred at 110° under nitrogen for 3 hours. R$_f$(VII, R$^{21}$=CH$_3$, R$^{20}$=t-BuPh$_2$Si)=0.61 (cyclohexane/ethyl acetate=6:1), R$_f$ (VII)=0.32 (toluene/cyclohexane=7:3).

The mixture was then concentrated, the residue was taken up in dichloromethane, and the organic phase was washed with water, dried and concentrated. Purification was by chromatography (silica gel, toluene: cyclohexane=7:3). The product fractions were concentrated, and resulted in 5.8 g (11 mmol) of pale yellow oil VII (R$^{21}$=CH$_3$, R$^{20}$=t-BuPh$_2$Si)=67%.

MS (70 eV): m/e=528 (M$^+$), 471 (M$^+$—C$_4$H$_9$), 367 (M$^+$—CH$_3$OH—HI), 213, 167, 129, 91, 41.

$^1$NMR (270 MHz, CDCl$_3$): δ=1.10 (s; 9H, C(CH$_3$)$_3$), 1.66 (ddd, J$_{2,2}$=14.5, J$_{2,3}$=4.0 J$_{2,1}$=2.0 Hz; 1H, 2-H$_{ax}$), 1.85 (ddd, J=14.5, J$_{2,3}$=8.0, J$_{2,1}$=4.5 Hz; 1H, 2-H$_{eq}$), 3.28 (d, J=7.0 Hz; 2H, 6-CH$_2$), 3.47 (s; 3H, OCH$_3$), 4.07 (dddd, J$_{3,2}$=8.0, J$_{3,4}$=J$_{3,2}$=J$_{3,F}$=4.0 Hz; 1H, 3-H), 4.35 (dt, J$_{5,6}$=7.0, J$_{5,F}$=29.0 Hz; 1H, 5-H), 4.47 (dd, J$_{4,3}$=4.0, J$_{4,F}$=47.0 Hz; 1H; 4-H), 4.71 (dd, J$_{1,2}$=4.5, J$_{1,2}$=2.0 Hz; 1H, 1-H), 7.30-7.50 (m; 5H, Aryl-H), 7.60-7.80 (m; 5H, Aryl-H).

EXAMPLE 8

2,4-Dichloro-6-(bis-4-fluorophenylmethyl)thiophenol
(formula VIII with X=S, $R^1$ and $R^3$=Cl, $R^2$=H,
$R^4$=H, $R^5$=bis-4-fluorophenylmethyl)

(a) 2,4-Dichloro-6-(bis-4-fluorophenylmethyl)phenol 6.4 g (34 mmol) of 1,2-dibromoethane were added dropwise to 0.85 g (35 mmol) of magnesium turnings in diethyl ether, and the mixture was refluxed for 1 hour. This solution was added dropwise to a Grignard solution made from 0.85 g (35 mmol) of magnesium and 6 g (34 mmol) of 4-fluorobromobenzene in diethyl ether, and then 7 g (19.5 mmol) of 4,6-dichloro-2-(4-fluorobenzoyl)phenol (cf. Houben-Weyl, Methoden der organischen Chemie (Methods of organic chemistry), volume 7/2a, 1973) were added, and the mixture was refluxed for 4 hours. It was then hydrolyzed with ice/HCl and extracted with ether, and the organic phase was dried and the solvent was distilled off. 8.3 g (16 mmol) (84%) of product were obtained, and this was dissolved in 500 ml of glacial acetic acid, and 5 ml of concentrated HCl were added. After addition of 1 g of catalyst (10% Pd/charcoal), hydrogenation was carried out in a shaken vessel until the theoretical amount of hydrogen had been absorbed. TLC check: $R_f$ (Grignard product)=0.16, $R_f$ (phenol)=0.38 (cyclohexane:ethyl acetate=5:1).

Purification was by chromatography on about 1000 g of silica gel (cyclohexane:ethyl acetate=5:1). Yield: 6.9 g (83%) of white phenol.

MS (70 eV): m/e=364 (M+), 269 (M+-95), 161.

$^1$H (60 MHz, CDCl$_3$): δ=5.2 (s; 1H, OH), 5.8 (s; 1H, Benzyl-H), 6.6–7.4 (m; 10H, Aryl-H).

(b) 4,6-Dichloro-2-[bis(4-fluorophenyl)methyl]phenyl N,N-dimethylthiocarbamate 3.6 g of 50% sodium hydride were suspended in 60 ml of absolute DMF. 29.2 g (80 mmol, 1 equivalent of 4,6-dichloro-2-[bis(4-fluorophenyl)methyl] phenol from stage (a) were introduced while cooling in ice, and the solution was stirred at room temperature for 30 min and cooled to 0° C. A solution of 12.4 g (1.25 equivalents) of dimethylthiocarbamoyl chloride (Aldrich) in 20 ml of DMF was added, and the reaction mixture was stirred at 80° C. for 2 h. It was cooled and then diluted with 500 ml of ether, and the solution was washed twice with water and once with potassium bicarbonate solution, and dried over magnesium sulfate, and the solvent was removed in vacuo. The residue was recrystallized from methanol. 32.3 g (89% yield) of the ester were obtained, melting point 178°-179° C.

MS: C$_{22}$H$_{17}$Cl$_2$NOS, 451/453 (M+), 416 (M+—Cl), 347/349.

$^1$H-NMR (CDCl$_3$, 60 MHz): δ=3,0 (s, 3H, CH$_3$); 3,5 (s, 3H, CH$_3$), 5,6 (s, 1H, CH), 6,7 (d, 1H, arom. H), 7,0 (s, 4H, arom. H), 7,1 (s, 4H, arom. H), 7,4 (d, 1H, arom. H).

(c) S-<4,6-Dichloro-2-[bis(4-fluorophenyl)methyl] phenyl> N,N-dimethylthiocarbamate 32 g of the compound from stage b were dissolved in 320 ml of sulfolane and heated under nitrogen at 250° C. until reaction was complete (about 2 h) and, after cooling, 100 ml of water were added and the mixture was extracted with ether. The dried organic phase was concentrated, and the product was crystallized from hexane. 25.5 g (80%) of the title compound were obtained, melting point 130°-131° C. (hexane).

$^1$H-NMR (CDCl$_3$, 60 MHZ): δ=3.0 (s, 6H, N(CH$_3$)$_2$); 6.1 (s, 1H, CH); 6.85 (d, 1H, Aryl-H); 6.95 (s, 4H, Aryl-H); 7,1 (s, 4H, Aryl-H); 7,5 (d, 1H, Aryl-H).

(d) 4,6-Dichloro-2-[bis(4-fluorophenyl)methyl] thiophenol

A solution of 6.2 g of S-[4,6-dichloro-2-[bis(4-fluorophenyl)methyl]phenyl] N,N-dimethylthiocarbamate from stage (c) in ether was added dropwise, while cooling in ice, to a suspension of 0.8 g of lithium aluminum hydride in absolute ether. The mixture was stirred at room temperature for 90 min and was hydrolyzed, while cooling in ice, with 2 N sulfuric acid (pH 3). It was extracted several times with ether, the solution was dried over magnesium sulfate, and the solvent was removed in vacuo. The thiophenol remained as residue (5.3 g of viscous oil, 100% yield) and was pure by TLC (100% toluene, $R_f$=0.66); melting point 95° C.

MS: C$_{19}$H$_{12}$Cl$_2$F$_2$S, 380/382 (M+), 283/285.

$^1$H-NMR (CDCl$_3$, 60 MHz): δ=4,0 (s, 1H, SH), 5,6 (s, 1H), Methine-H); 6,55 (d, J=2,5 Hz, 1H, arom.-H), 6.85 (s, 4H, arom.-H), 6.95 (s, 4H, arom.-H), 7.25 (d, J=2,5 Hz, 1H, arom.-H)

EXAMPLE 9

2,4,6-Trideoxy-6-(2,4-dichloro-6-(bisparafluorophenylmethyl)phenylthio)-4(R)-fluoro-3(S)-O-tertiary-butyldiphenylsilyl-α-methyl-D-gulopyranoside (formula IX with X=S, $R^{20}$=t-butyldiphenylsilyl, $R^{21}$=methyl, $R^1$ and $R^3$=Cl, $R^2$ and $R^4$=H,
$R^5$=bis-4-fluorophenylmethyl)

1.40 g (0.0037 mol) of thiophenol from Example 8 and 1.40 g (0.0037 mol) of iodide VII from Example 7 were introduced into 50 ml of absolute DMSO, 1.00 g (0.0078 mol) of dry K$_2$CO$_3$ was added, and the mixture was stirred at 50° C. for 6 h and then at 80° C. for 6 h. It was then concentrated, the residue was partitioned between ether and water, and the organic phase was dried and concentrated in a rotary evaporator. 1.73 g (0.0027 mol)=73% of a pale yellow oil were obtained; TLC (toluene, silica gel); $R_f$ (title compound IX)=0.21, $R_f$ (VII, compound from Example 7) 0.19, $R_f$ (thiophenol)=0.75.

$^1$H-NMR (60 MHz, CDCl$_3$): δ=1.1 (s; 9H, C(CH$_3$)$_3$), 2.6–3.0 (m; 4H, 2-H$_2$, 6-H$_2$), 3.40 (s; 3H, OCH$_3$), 4.0–4.5 (m; 3H, 3-H, 4-H, 5-H), 4.7 (dd, J=4.5, J=2.5 Hz; 1H, 1-H), 6.5 (s; 1H, Benzyl-H), 6.8 (d, J=4Hz; 1H, Aryl-H), 6.9–7.0 (m, AA'BB'System and d, J=4Hz; 9H, Aryl-H), 7.3–7.5 (m; 5H, Aryl-H), 7.6–7.8 (m; 5H, Aryl-H).

MS (DCI/Isobutane): m/e=749 (M+—OCH$_3$), 575, 378, 199, 93.

EXAMPLE 10

2,4,6-Trideoxy-6-(2,4-dichloro-6-(bisparafluorophenyl-methyl)phenylthio)-4(R)-fluoro-3(S)-O-tertiary-butyl-diphenylsilyl-D-gulopyranose (formula X with X=S, $R^{20}$ =t-$C_4H_9Ph_2Si$, $R^1$ =$R^3$=Cl, $R^2$=$R^4$=H, $R^5$=bis-4-fluorophenylmethyl)

1.25 g (0.0016 mol) of lactol ether from Example 9 (formula IX) were introduced into 40 ml of tetrahydrofuran, and 10 ml of water and 12 ml of concentrated hydrochloric acid were added, and the mixture was stirred at 60° C. for 10 h. It was then neutralized with solid $NaHCO_3$, insolubles were removed by filtration, and the filtrate was concentrated in a rotary evaporator. The remaining oil was purified by chromatography (200 g of silica gel 60, cyclohexane:ethyl acetate=4:1). 413 mg (0.00054 mol)=33% of an oil were obtained.

TLC (silica gel 60, cyclohexane:ethyl acetate=4:1): $R_f$(IX from Example 9)=0.61, $R_f$ title compound) 0.32 and 0.33.

$^1$H-NMR (270 MHz, $CDCl_3$): δ=1.06, 1.08 (s; 9H, $C(CH_3)_3$), 1.50–2.05 (m; 2H, 2-$H_2$), 2.70–2.90 (m; 2H, 6-$H_2$), 3.90–4.40 (m; 3H, 3-H, 4-H, 5-H), 4.95–5.30 (m; 2H, 1-H and OH), 6.45, 6.46 (s; 1H, Benzyl-H), 6.79 and 6.83 (d, J=4 Hz; 0.6 and 0.4H, Aryl-H), 6.90–7.05 (m; AA'BB'-System, 8-H, Aryl-H), 7.30–7.75 (m; Aryl-H).

MS (70 eV): m/e=748 ($M^+$—$H_2O$), 709 ($M^+$—$C_4H_9$), 691 (748-$C_4H_9$), 561, 378, 283, 199, 109.

EXAMPLE 11

6-(2,4-Dichloro-6-(bisparafluorophenylmethyl)phenyl-thio)-4(R)-fluoro-5(S)-hydroxy-3(S)-tertiary-butyl-diphenyl-silyloxyhexanoic acid lactone (formula XI with X=S, $R^1$ and $R^3$=Cl, $R^2$ and $R^4$=H, $R^5$=bis-4-fluorophenylmethyl, $R^{20}$=t-Bu-$Ph_2Si$)

0.54 mmol (0.413 g) of the hemiacetal from Example 10 in 10 ml of absolute dichloromethane was added dropwise to a suspension of 3.2 mmol (6 equivalents) of N-iodosuccinimide and 0.6 mmol (1 equivalent) of tetrabutylammonium iodide in 10 ml of dichloromethane at room temperature. The reaction was complete after 15 min. The mixture was diluted with 30 ml of dichloromethane and extracted with 2×50 ml of ten percent sodium thiosulfate solution, the organic phase was dried over magnesium sulfate and concentrated, and the product was purified by chromatography (silica gel cyclohexane:ethyl acetate=4:1). The product fractions (180–400 ml) were concentrated. 333 mg (0.44 mmol)=81% of a colorless oil were obtained, $R_f$(cyclohexane:ethyl acetate 4:1)=0.40.

$^1$H-NMR (270 MHz, $CDCl_3$): δ=1.00 (s; 9H, $C(CH_3)_3$), 2.51 (ddd, $J_{2,2}$=17.0 Hz, $J_{2,3}$=3.0 Hz=$J_{2,F}$; 1H, 2 $H_{ax}$), 2.64 (ddd, $J_{2,2}$=17.0, $J_{2,3}$=4.0 Hz=$J_{2,4}$; 1H, 2-$H_{eq}$), 2.87 (dd, $J_{6,6}$=13.0 Hz, $J_{6,5}$=8.0 Hz; 1H, 6-Ha), 3.05 (dd, $J_{6,6}$=13.0, $J_{6,5}$=6.0 Hz; 1H, 6-H$_b$), 4.28 (dddd, $J_{3,2}$=3.0, $J_{3,2}$=4.0 Hz=$J_{3,4}$=$J_{3,F}$; 1H, 3-H), 4.44 (ddd, $J_{4,F}$=47.0, $J_{4,3}$=4.0, $J_{4,5}$=1.5 Hz, 1H, 4-H), 4.71 (dddd, $J_{5,F}$=31.0, $J_{5,6}$=8.0, $J_{5,6}$=6.0, $J_{5,4}$ 1.5 Hz; 1H, 5-H), 6.45 (s; 1H, Benzyl-H), 6.82 (d, J 2 Hz; 1H, Aryl-H), 6.95–7.05 (m; 9H, Aryl-H), 7.35–7.65 (m; 10H, Aryl-H).

MS (DCI/Isobutane): 765 ($M^+$+H); 707 ($M^+$—$C_4H_9$), 687 (707-HF), 378 (thiophenol fragment), 309, 225, 198 (100%, $(Ph)_2$+—$BuSiO^+$).

EXAMPLE 12

6-(2,4-Dichloro-6-(bisparafluorophenylmethyl)phenyl-thio)-3(R),5(S)-dihydroxy-4(R)-fluorohexanoic acid lactone (formula I, X-Y=S—$CH_2$, R=2-(bis-4-fluorophenylmethyl)-4,6-dichlorophenyl).

200 mg (0.26 mmol) of lactone from Example 11 were dissolved in 10 ml of THF, and 1.6 mmol (0.094 g=0.089 ml) of glacial acetic acid and 0.8 mmol (0.252 g) of tetrabutylammonium fluoride trihydrate were added, and the mixture was stirred at room temperature for 14 h. It was then concentrated, and the residue was taken up in 2 ml of methylene chloride and purified by chromatography (20 g of silica gel 60, cyclohexane:ethyl acetate=2:1). The product fractions (240–360 ml) were combined: Yield 130 mg (0.25 mmol)=95%, white solid, melting point 75° (ether); $[\alpha]_D$=+7.3° (C=1, $CHCl_3$). $R_f$ (cyclohexane:ethyl acetate=1:1)=0.36.

$^1$H-NMR (270 MHz, $CDCl_3$): δ=2.61 (dddd, $J_{2,2}$=17.8, $J_{2,3}$=3.0=$J_{3,F}$, $J_{2,4}$=0.8 Hz; 1H, 2-$H_{ax}$), 2.86 (ddd, $J_{2,2}$=17.8, $J_{2,3}$=4.5, $J_{2,OH}$=3.5 Hz; 1H, 2-$H_{eq}$), 2.98 (dd, $J_{6,6}$=14.0, $J_{6,5}$=7.0 Hz; 1H, 6-Hb), 3.02 (ddd, $J_{6,6}$=14.0, $J_{6,5}$=7.0, $J_{6,F}$=1.0 Hz; 1H, 6-Hb), 4.41 (dddd, $J_{3,2}$=4.5, $J_{3,2}$=3.0, $J_{3,4}$=4.0, $J_{4,F}$=5.0 Hz; 1H, 3-H), 4.45 (dddt, $J_{5,6}$=7.0, $J_{5,4}$=1.5, $J_{5,F}$=31.0 Hz; 1H, 5-H), 4.67 (dddd, $J_{4,F}$=47.0, $J_{4,3}$=4.0, $J_{4,5}$=1.5, $J_{4,2}$=0.8 Hz; 1H, 4-H), 6.40 (s; 1H, Aryl-H), 6.82 (D, J 2.0 Hz; 1H, Aryl-H), 7.00 (AA'BB'-System, 8H, Aryl-H), 7.44 (d, J 2Hz; 1H, Aryl-H).

$^{19}$F-NMR ($CDCl_3$, $CFCl_3$ Standard, 282 MHz): δ=−115.83 (tt, J=6.9, J=7.0 Hz; 1F, Aryl-F), −115.92 (tt, J=6.9, J=6.9 Hz; 1F, Aryl-F9, −207.25 (ddddd, J=46.8, J=30.4, J=5.1, J=3.5, J=3.4 Hz; 1F, 4-F).

$^{13}$C-NMR ($CDCl_3$, 100.6 MHz): δ=34.4 (C-6), 35.2 (C-2, J($^{13}$C,F)=5 Hz), 53.9 (Benzyl-C), 65.9 (C-3, $J_{3,F}$=28 Hz), 75.8 (C-5, $J_{5,F}$=18 Hz), 86.0 (C-4, $J_{4,F}$=182 Hz), 115.5, 115.6, 115.7, 115.8, 128.9, 129.1, 130.9, 131.0, 135.7, 138.1, 138.2, 151.7 (aromatic-C), 167.0 C=0).

EXAMPLE 13

Sodium 6(S)-[2,4-dichloro-6-(bis-4-fluorophenylmethyl)phenyl-thio]-4(R)-fluoro-3(S),5(S)-dihydroxyhexanoate (formula II, Na salt)

0.044 mmol (0.0232 g) of lactone I from Example 12 was dissolved in 2 ml of ethanol, 0.044 mmol (44 μl of a 1 M NaOH) of sodium hydroxide solution was added, and the mixture was stirred at room temperature for 2 h. It was then evaporated to dryness and dried under high vacuum. 25.0 mg (0.044 mmol)=100% of sodium salt were obtained as a solid.

TLC (chloroform:methanol=4:1): $R_f$(I)=0.77, $R_f$(II sodium salt)=0.22.

EXAMPLE 14

3-O-Benzyl-2,4,6-trideoxy-4(R)-fluoro-6-iodo-α-methyl-D-gulopyranoside (formula VII with $R^{20}$=benzyl, $R^{21}$=CH$_3$, 4(R)-fluoro)

The title compound was synthesized in analogy to Examples 1 to 7 with the difference that the steps in the synthesis as in Example 7, steps a and b, are omitted. The yield at the corresponding step in the synthesis of Example 7 c, α, β, γ is 60% over three stages. The title compound is obtained as a pale yellow oil.

TLC: $R_f$ (cyclohexane:ethyl acetate=4:1)=0.37, $R_f$ (toluene/cyclohexane=7:3)=0.11.

$^1$H-NMR (270 MHz, C$_6$D$_6$): δ=1.55-1.80 (m, ABMX System, AB-part; 2H, 2-H$_2$), 2.93 (dd, J$_{6,6}$=11.0, J$_{6,5}$=5.5 Hz; 1H, 6-H$_a$), 3.18 (ddd, J$_{6,6}$=11.0, J$_{6,5}$=9.0 Hz; J=1.2 Hz; 1H, 6-H$_b$), 3.23 (s; 3H, OCH$_3$), 3.52 (dddd, J$_{3,F}$=10.0, J$_{3,2}$=J$_{3,2}$=J$_{3,4}$=4.0 Hz; 1H, 3-H), 4.19 (ddd, J$_{5,F}$=30.0, J$_{5,6}$=5.5, J$_{5,6}$=9.0 Hz; 1H, 5-H), 4.27 (m; AB-System; Benzyl-CH$_2$), 4.34 (dd, J$_{4,F}$=47.0, J$_{4,3}$=4.0 Hz; 1H, 4H), 4.46 (dd, J$_{1,2}$=2.5, J$_{1,2}$=4.5 Hz; 1H, 1-H), 7.05-7.3 (m; 5H, aromatic-H).

EXAMPLE 15

3-O-Benzyl-2,4,6-trideoxy-4(R)-fluoro-6-triphenylphosphonio-α-methyl-D-gulopyranoside iodide (formula XII with $R^{20}$=benzyl, and $R^{21}$=CH$_3$).

1.0 g (0.0026 mol) of 6-iodo-D-guloside from Example 14 and the equivalent amount of triphenylphosphine were stirred while being converted into a melt which was stirred at this temperature (80° C.) under N$_2$ until reaction was complete. The product was then taken up in a little dichloromethane, and the salt was precipitated by addition of toluene. The salt was filtered off with suction and then dried under high vacuum (1.6 g, 95%). TLC (CHCl$_3$:CH$_3$OH=10:1)=0.41.

$^1$H-NMR (270 MHz, CDCl$_3$): δ=1.75-1.90 (m; 1H, 2-H$_{ax}$), 1.95-2.10 (m; 1H, 2-H$_{eq}$), 2.35 (s; 0.35×3H, β-OCH$_3$), 2.59 (s; 0.65×3H, α-OCH$_3$), 3.50-3.70 (m; 1H, 6-H$_a$), 3.75-3.95 (m, 1H, 6-H), 4.27 (dd, J=6 Hz; J=7 Hz; 0.35 H, β-1-H), 4.52 (dd, J=3, J=5 Hz; 0.65 H, α-1-H), 4.75 (AB-System; Benzyl-CH$_2$O), 5.19 (dd, J=3, J=31 Hz; 1H, 5-H), 5.38 (dd, J=4, J=47 Hz; 1H, 4-H), 7.10-7.40 (m, 5H, Aryl-H), 7.60-7.95 (m; 15H, Aryl-H).

MS (70eV): m/e=(515, M+), 262, 183.

EXAMPLE 16

2-Butyl-4,6-dichlorobenzaldehyde (formula XIIIa with Z=single bond, $R^7$=butyl, $R^8$=$R^9$=Cl)

The synthesis was carried out in analogy to statements in the literature (Stokker et al., J. Med. Chem. 29 (1986), 173), starting from 2,4-dichlorobenzaldehyde, reaction with aniline to give the corresponding anilide, conversion into a palladium complex and coupling with butylmagnesium bromide with the addition of triphenylphosphine. After the coupling was complete, most of the triphenylphosphine was removed by cooling the ethereal reaction solution to −78° C., and analytically pure product was obtained by chromatography (silica gel 60, cyclohexane: ethyl acetate=100:1).

TLC (cyclohexane/ethyl acetate=4:1): $R_f$=0.56.

$^1$H-NMR (60 MHz, CDCl$_3$): δ=0.7-1.1 (t, J 6 Hz; 3H, CH$_3$), 1.5 (m$_c$; 4H, CH$_2$—CH$_2$), 2.9 (t, J 7 Hz; Benzyl-CH$_2$), 7.1-7.5 (m; 2H, Aromatic-H), 10.6 (s; 1H, CHO).

EXAMPLE 17

3-O-Benzyl-7-(2-n-butyl-4,6-dichlorophenyl)-6,7-dideoxy-4(R)-fluoro-α-methyl-D-gulohept-6E-enopyranoside (formula XIV, R=2-n-butyl-4,6-dichlorophenyl, $R^{20}$=benzyl, $R^{21}$=methyl)

1 mmol (0.643 g) of phosphonium salt from Example 15 was dried under high vacuum and then dissolved in 5.0 ml of THF/HMPTA (2:1 v/v), and the solution was cooled to −60° C. under nitrogen and 1 mmol of n-BuLi (0.72 ml of an approx. 1.4 M solution in hexane) was added dropwise. After 30 seconds, after the BuLi addition was complete, 1.5 mmol (0.347 g) of aldehyde (from Example 16) was added dropwise within 1 min, and the mixture was allowed to warm to −10° C. in 45 minutes. 20 ml of petroleum ether were added, the mixture was filtered, the filtrate was concentrated, and the product was purified by chromatography (silica gel 60, hexane/ethyl acetate=5:1). The fractions containing product of $R_f$=0.41 (cyclohexane/ethyl acetate=4:1) were collected and concentrated. 215 mg (0.46 mmol)=46% of colorless oil were obtained.

TLC: $R_f$ (phosphonium salt, Example 15)=0.01, $R_f$ (aldehyde from Example 16)=0.56, $R_f$ (product)=0.41 (cyclohexane:ethyl acetate=4:1).

$^1$H-NMR (270 MHz, CDCl$_3$): δ=0.92 (t, J=7 Hz; 3H, CH$_3$), 1.25-1.45 (m; 2H, CH$_2$), 1.45-1.60 (m; 2H, CH$_2$), 2.00 (ddd, J$_{2,2}$=14 Hz, J$_{2,3}$=4Hz, J$_{2,1}$=2.5 Hz; 1H, 2 H$_{ax}$), 2.11 (m$_c$; 1H, 2 H$_{eq}$), 2.63 (dd, J=6 Hz, J=8H; 2H, Benzyl-H$_2$), 3.43 (s; 3H, OCH$_3$), 3.88 (dddd, J$_{3,F}$=10 Hz, J$_{3,2}$=4 Hz, J$_{3,2}$=4Hz, J$_{3,4}$=4 Hz; 1H, 3-H), 4.40-4.55 (m; 1H, 5-H), 4.68 (AB-System; 2H, Aryl-CH$_2$O), 4.69 (dd, J$_{4,F}$=47 Hz, J$_{4,3}$=4Hz; 1H, 4-H), 4.89 (dd, J=4.5 Hz, J$_{1,2}$=2.5 Hz; 1H, 1-H), 5.94 (dd, J$_{6,5}$=6Hz, J$_{trans}$=16 Hz; 1H, 6-H), 6.64 (d, J$_{trans}$=16 Hz; 1H, 7-H), 7.08 (m; 1H, Aryl-H), 7.20-7.40 (m; 6H, Aryl-H).

EXAMPLE 18

7-(2-n-Butyl-4,6-dichlorophenyl)-3(S),5(R)-dihydroxy-4(R)-fluoro-E-hept-6-enoic acid lactone (formula I with X-Y=CH=CH, R=2-butyl-4,6-dichlorophenyl)

The benzyl protective group was removed, without saturation of the double bond, using Pearlman's catalyst and as specified in the literature (Prugh et al., J. Org. Chem. 51 (1986) 60, 651, 654) using the following procedure:

467 mg (1.0 mmol) of the compound from Example 17 were refluxed in 20 ml of ethanol with the addition of 20% Pd(OH)$_2$/C (100 mg) for 50 hours and, after concentration and chromatography, 168 mg (0.43 mmol)=43% of the debenzylated compound were obtained. This was reacted, without further purification, as in Example 10, and the resulting product (150 mg) was oxidized as in Example 11 by oxidation with N-iodosuccinimide/tetrabutylammonium iodide to give the lactone of the title compound.

TLC (cyclohexane:ethyl acetate=4:1) $R_f$ (Example 17)=0.41, $R_f$(title compound)=0.01.

$^1$H-NMR (60 MHz, CDCl$_3$): $\delta$=0.9 (t, J=7 Hz; 3H, CH$_3$), 1.2-1.6 (m; 4H, CH$_2$—CH$_2$), 2.5-3.1 (m; 4H, 2-H$_2$, Benzyl-H$_2$), 4.3-4.5 (m; 2H, 3-H, 5-H), 4.7 (d, J=47 Hz; 1H, 4-H), 6.0 (dd, J=16 Hz, J=6 Hz; 1H, 6-H), 6.6 (d, J=16 Hz; 1H, 7-H), 7.1-7.2 (m; 2H, Aryl-H).

EXAMPLE 19

2,4,6-Trideoxy-3-O-t-butyldiphenylsilyl-4(S)-fluoro-6-iodo-α-methyl-D-gulopyranoside (formula VII with $R^{20}$=t-BuPh$_2$Si, $R^{21}$=CH$_3$)

(a) (α) Methyl-3-O-benzyl-4,6-di-O-acetyl-2-deoxy-D-gulopyranoside (formula XXI, Scheme 1)

3.10 g (10 mmol) of anhydrous sugar XIX from Example 5, 5.25 g (20 mmol) of triphenylphosphine and 1.84 g (10 mmol) of anhydrous zinc acetate were introduced under nitrogen into 40 ml of absolute toluene, and the mixture was cooled to 0° C. and stirred vigorously (suspension). To this were added dropwise 20 mmol (3.48 g=3.15 ml) of diethyl azodicarboxylate, and the mixture was allowed to reach room temperature. Since reaction was incomplete after 4 h, a further 10 mmol of ZN(OAc)$_2$ and 20 mmol of azodicarboxylate were added, and the mixture was stirred for 15 h. Then 40 ml of ether and 10 ml of hexane were added, insolubles were removed by filtration, and the product was purified by chromatography (200 g of silica gel, cyclohexane:ethyl acetate=2:1). 2.3 g (6.5 mmol)=65% of colorless oil were obtained, $R_f$ (title compound)=0.47, $R_f$ (XIX from Example 5)=0.33 (cyclohexane:ethyl acetate=1:1).

$^1$H-NMR (270 MHz, CDCl$_3$): $\delta$=1.95 (m$_c$; 2H, 2-H$_2$), 2.05, 2.10 (s; 6H, COCH$_3$), 3.41 (s; 3H, OCH$_3$), 3.63 (ddd, $J_{3,2}$=$J_{3,2}$=$J_{3,4}$=4 Hz; 1H, 3-H), 4.12 (m$_c$; 2H, 6-H$_2$), 4.47 (dt, $J_{5,6}$=7 Hz; $J_{5,4}$=1 Hz; 1H, 5-H), 4.65 (AB-System; Benzyl-CH$_2$O), 4.79 (dd, $J_{4,3}$=4 Hz, $J_{4,5}$=1 Hz; 1H, 4-H), 4.93 (dd, $J_{1,2}$=3.5, $J_{1,2}$=1.5 Hz; 1H, 1-H), 7.30-7.45 (m; 5H, Aryl-H).

(b) The compound from stage a was converted by elimination of the acetate protective groups in analogy to Example 7, stage c/α and acetylation of the 6-OH group as in Example 5 b into the 6-monoacetate XXII with inverse configuration at C-4 and was then converted in accordance with Examples 6 and 7 into the 4(S)-fluoro derivative (α-fluoro).

EXAMPLE 20

6-(2,4-Dichloro-6-(bisparafluorophenylmethyl)phenyl-thio)-3(S),5(S)-dihydroxy-4(R)-fluorohexanoic acid lactone (formula I with X-Y=S—CH$_2$, R=2,4-dichloro-6-(bisparafluorophenylmethyl)phenyl)

4,6-Di-O-acetyl-3-O-benzyl-2-deoxy-α-methyl-D-gulopyranoside from Example 19a was converted into the fluoro lactone in accordance with Examples 6, 7, 9, 10, 11 and 12. Colorless oil, $R_f$=0.36 (cyclohexane:ethyl acetate=1:1).

$^1$H-NMR (270 MHz, CDCl$_3$) $\delta$=2.6 (m; 1H, 2-H$_{ax}$), 9.9 (m, 1H, 2-H$_{eq}$), 3.0 (m; 2H, 6-H$_2$), 4.4 (m; 1H, 1-H), 6.4 (s; 1H, Aryl-H), 6.8 (m; 1H, Aryl-H), 7.0 (m, AA'BB'-system; 8H, Aryl-H), 7.4 (m; 1H, Aryl-H).

EXAMPLE 21

3-Hydroxymethyl-2-isopropyl-4-p-fluorophenyl-6-phenylpyridine

The compound was prepared from the corresponding ethyl pyridine-3-carboxylate by reduction with LiAlH$_4$. The ethyl pyridine-3-carboxylate had been obtained by Michael addition of ethyl 4-methyl-3-ketopentanoate onto 1-phenyl-3-parafluorophenylprop-2-enone and reaction of the product with ammonium acetate/FeCl$_3$/glacial acetic acid by the procedure of F. Rehberg, F. Krohnke, Lieb. Ann. Chem. 717 (1968) 91.

14 g (0.039 mol) of ethyl 2-isopropyl-4-parafluorophenyl-6-phenylpyridine-3-carboxylate were introduced into 300 ml of absolute THF in a 2 l 3-neck flask and, while excluding moisture, 1.4 g (0.039 mol) of LiAlH$_4$ were added. The mixture was stirred at room temperature for 4 h until reaction was complete. Then 100 ml of water were cautiously added dropwise, and the mixture was extracted with ether. The ether phase was dried (MgSO$_4$) and concentrated and then the product was crystallized from cyclohexane.

Yield: 8 g (0.025 mol)=64% of white crystals of melting point 165° C.

TLC: $R_f$ (ester)=0.51, $R_f$ (alcohol)=0.23 (Ethyl acetate:cyclohexane=1:4).

EXAMPLE 22

2-Isopropyl-4-parafluorophenyl-6-phenylpyridine-3-aldehyde (formula XIIIb, $R^{10}$=isopropyl, $R^{11}$=p-fluorophenyl, $R^{12}$=phenyl, A=CH)

13.3 g (0.062 mol) of pyridinium chlorochromate and 10 g of ground 4 A molecular sieves were introduced into 200 ml of absolute CH$_2$Cl$_2$. 10 g (0.031 mol) of the pyridine alcohol from Example 21 were added at room temperature, and the mixture was then stirred for 1 h until reaction was complete (TLC). 500 ml of dry ether were added, and the mixture was filtered through about 100 g of Florisil (column 4×30 cm), washing with 200 ml of CH$_2$Cl$_2$. The combined organic phases were concentrated, and the residue was crystallized from isopropanol.

Yield: 8 g (0.025 mol)=81% of white needles of melting point 98° C.

$^1$H-NMR (60 MHz, CDCl$_3$): $\delta$=1.40 (d, J=7.0 Hz; 6H, CH(CH$_3$)$_2$), 4.0 (hep, J=7.0 Hz; 1H, C$\underline{H}$ Me$_2$), 7.6-7.0 (m; 8H, Aryl-H), 8.4-8.0 (m; 2H, Aryl-H), 10.1 (s; 1H, CHO).

MS (E$^J$): m/e=319 (M$^+$), 290 (M$^+$—CHO), 276 (M$^+$—C$_3$H$_7$), 263 (276—CH).

EXAMPLE 23

2,4-Dimethyl-6-parafluorophenylbenzaldehyde (formula XIIIa, $R^7$=parafluorophenyl, Z=single bond, $R^8$=o-methyl, $R^9$=methyl)

The compound was prepared as described by Stokker, G. E. et al., J. Med. Chem. 29 (1986) 170-181.

Yield: 79%, melting point 80-81° C. (sublime).

$^1$H-NMR (60 MHz, CDCl$_3$): $\delta$=2.32 (s; 3H, CH$_3$), 2.58 (s; 3H, CH$_3$), 6.7-7.2 (m; 6H, Aryl-CH) 9.65 (s; 1H, CHO).

EXAMPLE 24

2-para-fluorophenyl-6-isopropyl-4-phenylbenzaldehyde. (Formula XIIIa, $R^7$=isopropyl, Z=single bond, $R^8$=o-para-fluorophenyl, $R^9$=phenyl)

The compound was prepared from 4-phenylbenzaldehyde (Aldrich) by repeated triphenylphosphine-catalyzed addition of 4-fluorophenylmagnesium bromide and isopropylmagnesium bromide onto the palladium acetate of the appropriate anilineimine by the method of Murahashi, J. Org. Chem. 43 (1978) 4099, as described by Stokker, G. E., J. Med. Chem. 29 (1986) 170-181.

Yield: 75%, white needles of melting point 109–110° C.

$^1$H-NMR (60 MHz, CDCl$_3$): 1.30 (d, J O 7.0 Hz; 6H, CH(CH$_3$)$_2$); 3.90 (sept., J=7.0 Hz, 1H, CH(CH$_3$)$_2$), 7.70–6.70 m; 11H, Aryl-H, 9.75 (s; 1H, CHO).

EXAMPLE 25

4,6-O-Benzylidene-2-deoxy-3-O-paramethoxybenzyl-α-methyl-D-allopyranoside (formula XVII, $R^{20}$=p-methoxybenzyl, $R^{21}$=methyl)

150 g (0.56 mol) of 4,6-O-benzylidene-2-deoxy-α-methyl-D-allopyranoside from Example 4 were added in portions to 70.0 g (1.6 mol) of a 55% suspension of sodium hydride in mineral oil in 3.8 l of absolute DMF at room temperature (also abbreviated to RT) under nitrogen, and the mixture was stirred at 45° C. for 30 min and then cooled to RT, and 107.0 ml (123.6 g≐0.79 mol) of para-methoxybenzyl chloride were added dropwise. The mixture was stirred at 80° C. for 3 h, allowed to cool, 30 ml of water were added cautiously, and the solvent was removed by distillation under high vacuum (0.1 mm, 40° C.). The residue was dissolved in methylene chloride and washed with water. The organic phase was dried (MgSO$_4$) and concentrated. The residue was crystallized from diisopropyl ether. 190 g (0.49 mol)≐87% of colorless crystals were obtained, melting point 85°-86° C. R$_f$ (product)=0.49, R$_f$ (precursor)=0.27 (cyclohexane:ethyl acetate=1:1). $[\alpha]_D^{20}$= +42.7° , c=1.15, CHCl$_3$.

$^1$H-NMR (270 MHz, CDCl$_3$): δ=1.90 (ddd, J=15 Hz, J=4 Hz, J=6 Hz; 1H, 2-Hax), 2.17 (dd, J=15 Hz, J=3 Hz; 1H, 2-Heq), 3.40 (s; 3H, 1-α-OCH$_3$), 3.60–3.75 (m; 2H, 6-H$_2$), 3.80 (s; 3H, Aryl-OCH$_3$), 3.94 (ddd, J=J=3 Hz, J=4Hz; 1H, 3-H), 4.31 (dd, J=10 Hz, J=6 Hz; 1H, 4-H), 4.43 (m; 1H, 5-H), 4.70 (d, J=5 Hz; 1H, 1-H), 4.75 (AB-System; 2H, Aryl-CH$_2$), 5.56 (s, 1H, benzylidene-H),6.85 and 7.30 (AA'BB'-System; 4H), 7.30–7.60 (m; 5H, Aryl-H).

EXAMPLE 26

2-Deoxy-3-O-paramethoxybenzyl-α-methyl-D-allopyranoside (formula XVIII, $R^{20}$=p-methoxybenzyl, $R^{21}$=methyl)

0.19 g (0.001 mol, i.e. a 1 mM solution=0.02% by weight solution) of p-toluenesulfonic acid monohydrate was added to 50 g (0.13 mol) of the benzylidene acetal from Example 25 in one liter of absolute methanol at room temperature and stirred for 20 h. The mixture was neutralized with 5 ml of triethylamine and concentrated in vacuo. The product was purified by column chromatography (silica gel 60, cyclohexane:ethyl acetate=1:4 (1.2 l), ethyl acetate (2 l)). 38 g (0.127 mol)≐98% of an oil were obtained. R$_f$ (product)=0.17, R$_f$ (precursor)=0.62 (cyclohexane:ethyl acetate=1:4). $[\alpha]_D^{20}$=146.3° , c=1.0, CHCl$_3$.

$^1$H-NMR (270 MHz, CDCl$_3$): δ=1.75 (ddd, J=15 Hz, J=6 Hz, J=4 Hz; 1H, 2-Hax), 2.05 (t, J=6Hz; 1H, 6 -OH), 2.33 (dd, J=15 Hz, J=4 Hz; 1H, 2-Heq), 2.60 (d, J=12 Hz; 1H; 4-OH), 3.39 (s; 3H, 1-α-OCH$_3$), 3.58 (dt, J=10 Hz, J=4 Hz; 1H, 5-H), 3.82 (s; 3H, Aryl-OCH$_3$), 3.70–4.00 (m; 4H, 3H, 4H, 6-H$_2$), 4.33 and 4.75 (AB-System; 2H, Aryl-CH$_2$O), 4.74 (d, J=5 Hz; 1H,α-1-H), 6.90 and 7.4 (m$_c$, AA'BB'-System; 4H, Aryl-H).

EXAMPLE 27

6-O-Acetyl-2-deoxy-3-O-paramethoxybenzyl-α-methyl-D-allopyranoside (formula XIX, $R^{20}$=p-methoxybenzyl, $R^{21}$=methyl, $R^{22}$=acetyl)

33 ml (0.24 mol) of triethylamine and 420 ml of absolute dichloromethane were added to 29.5 g (0.099 mol) of the deoxyglycoside from Example 26, freshly dried in methylene chloride over calcium chloride. 10.3 ml (0.11 mol) of acetic anhydride were added dropwise to this solution, with exclusion of moisture, and the mixture was stirred for 16 hours. It was then washed with water, and the organic phase was dried over MgSO$_4$ and concentrated. 27 g (0.079 mol)≐81% of colorless oil were obtained after purification by chromatography (500 g of silica gel, cyclohexane:ethyl acetate=1:2). R$_f$ (product)=0.47, R$_f$ (precursor)=0.17 (cyclohexane:ethyl acetate=1:4). $[\alpha]_D^{20}$= +143.5° , c=1.0, CHCl$_3$.

$^1$H-NMR (270 MHz, CDCl$_3$): δ=1.77 (ddd, J=15 Hz, J=4.5 Hz, J=3.5 Hz; 1H, 2 Hax), 2.10 (s; 3H, COCH$_3$), 2.33 (ddd, J=15 Hz, J=3 Hz, J=1 Hz; 1H, 2-Heq), 2.64 (d (br), J=10 Hz; 1H, OH), 3.38 (s; 3H, 1-α-OCH$_3$), 3.57 (td, J=10 Hz, J=4.2 Hz; 1H, 5-H), 3.82 (s; 3H, Aryl-OCH$_3$), 3.87 (dt, J=3.5 Hz, J=3.0 Hz; 1H, 1-H), 4.06 (ddd, J=10.0 Hz, J=4.2 Hz, J=3.0 Hz; 1H, 4-H), 4.36 (m$_c$; 3H, 6-H$_2$ and A part of the aryl-CH$_2$-O AB system),4.74 (d, J=4.5 Hz; 1H, α-1-H), 4.75 (m$_c$; B part of the aryl-CH$_2$O AB system), 6.90 and 7.30 (m$_c$, AA'BB'-System; 4H, Aryl-H).

EXAMPLE 28

6-O-acetyl-2,4-dideoxy-4(R)-fluoro-3-O-paramethoxybenzyl-α-methyl-D-gulopyranoside (formula XXa, $R^{20}$=p-methoxybenzyl, $R^{21}$=methyl, $R^{22}$=acetyl)

19.3 g (0.120 mol) of diethylaminosulfur trifluoride (DAST) were added dropwise, while stirring and excluding moisture at −20° C., to 27 g (0.079 mol) of the allopyranoside from Example 27, 102 ml of ethyldiisopropylamine and 500 ml of absolute toluene, and the mixture was stirred for 10 min and then heated to 80° C. within half an hour. The mixture was stirred at this temperature for 4 h. It was then cooled to 0° C. and 50 ml of methanol were cautiously added dropwise. The mixture was then extracted three times with water. The organic phase was dried over MgSO$_4$ and concentrated. The product was purified by column chromatography on 1 kg of silica gel (cyclohexane:ethyl acetate=2:1).

17.3 g (0.051 mol)=64% of a pale yellow oil were obtained. $R_f$ (product)=0.47, $R_f$ (precursor)=0.20 (cyclohexane:ethyl acetate=1:1). $[\alpha]_D^{20} = +76.5°$, c=1.0, CHCl$_3$.

$^1$H-NMR (270 MHz, CDCl$_3$):δ=1.93 (ddd, J=15 Hz, J=5 Hz, J=3 Hz; 1H, 2-Hax), 2.05 (dddd, J=15 Hz, J=5 Hz, J=3Hz; 1H, 2-Heq), 2.10 (s; 3H, COCH$_3$), 3.39 (s; 3H, α-OCH$_3$), 3.78 (ddd, J=5 Hz, J=4Hz, J=5 Hz; 1H, 3-H), 6.90 and 7.30 (AB-System; 4H, Aryl-H), 3.80 (s, 3H, Aryl-OCH$_3$), 4.10–4.30 (m; 3H, 5-H, 6-H$_2$), 4.48 (dd, J=46 Hz, J=5 Hz; 1H, 4-H), 4.55 (AB-System; 2H, Aryl-CH$_2$O), 4.79 (dd, J=3.0 Hz, J=2.5 Hz; 1H, α-1-H.

$^{19}$F-NMR (94 MHz, CDCl$_3$, CFCl$_3$ int. Standard, δ(ppm)=0): δ=−206.0 (ddd, J=47 Hz, J=35 Hz, J=10 Hz; 1F, 4(R)-F).

MS (DCI, isobutane): m/e=341 (M—H), 310 (M—CH$_3$OH), 295 (310—CH$_3$), 121 (CH$_3$O—CH$_2$+).

EXAMPLE 29

2,4-Dideoxy-4(R)-fluoro-3-O-paramethoxybenzyl-α-methyl-D-gulopyranoside 88.7 ml of a 1 M methanolic solution of sodium methylate were added to 26.9 g (0.079 mol) of the 6-O-acetyl-gulopyranoside from Example 28 in 320 ml of absolute methanol at RT, and the mixture was stirred for 1 hour. 100 ml of the weakly acidic ion exchanger (®)Amberlite CG 50-II were then added to the solution, which was stirred vigorously for 2 min and filtered. The residue on the filter was washed with methanol, and the combined solutions were concentrated.

21.4 g (0.071 mol)=90% of a colorless oil were obtained, $R_f$ (product)=0.23, $R_f$ (precursor)=0.43 (cyclohexane:ethyl acetate=1:1). $[\alpha]_D^{20} = +76.5°$ C., c=1.0, CHCl$_3$.

$^1$H-NMR (270 MHz, CDCl$_3$):δ=1.95 (ddd, J=15 Hz, J=5 Hz, J=3 Hz; 1H, 2-Hax), 2.05 (dddd, J=15 Hz, J=5 Hz, J=5 Hz, J=3 Hz; 1H, 2-Heq), 3.41 (s; 3H, α-OCH$_3$), 3.70–3.92 (m, 6H, 3-H, 6-H$_2$ and Aryl OCH$_3$), 4.19 (ddd, J=32 Hz, J=8 Hz, J=4 Hz; 1H, 5-H), 4.49 (dd, J=46 Hz, J=5 Hz; 1H, 4-H), 4.56 (m$_c$, AB-System; 2H, Aryl-CH$_2$O), 4.81 (dd, J=3.0 Hz, J=2.5 Hz; 1H, α-1-H, 6.90 and 7.30 (AA'BB'-System; 4H, Aryl-H).

EXAMPLE 30

2,4,6-Trideoxy-4(R)-fluoro-6-iodo-3-O-paramethoxybenzyl-α-methyl-D-gulopyranoside (formula VII, R$^{20}$=para-methoxy-benzyl, R$^{21}$=methyl)

10.5 g (0.035 mol) of 4(R)-fluoro-3-O-p-methoxybenzylα-methyl-D-gulopyranoside from Example 29 were dissolved in 150 ml of absolute DMF, 11 ml of pyridine were added and, at −20° C. under argon, 24 g (0.053 mol) of methyltriphenoxyphosphonium iodide were added with exclusion of moisture. The mixture was stirred at this temperature for 3 hours. A polar intermediate was produced, $R_f$ (cyclohexane:ethyl acetate=1:1)=0.16. The mixture was allowed to warm to RT and then stirred for 2 hours, resulting in the main product with $R_f$=0.56, $R_f$(precursor)=0.21 (cyclohexane:ethyl acetate=1:1). 15 ml of methanol were added dropwise at 0° C. and, after 30 min, the mixture was concentrated in vacuo (<0.1 mm, 40° C.). The residue was taken up in ether, and the solution was washed with ice-cold 1N sodium hydroxide solution, 10% strength Na$_2$S$_2$O$_3$ solution and water. The organic phase was dried over Na$_2$SO$_4$ and concentrated. The product was purified by chromatography on 200 g of silica gel (toluene:cyclohexane:ethyl acetate=7:4:1). 11.6 g (0.028 mol)=81% of a pale yellow oil were obtained.

$^1$H-NMR (270 MHz, CDCl$_3$): δ=1,89 (ddd, J=15 Hz, J=5 Hz, J=3 Hz; 1H, 2-Hax), 2.01 (dddd, J=15 Hz, J=5 Hz, J=5 Hz, J=3 Hz; 1H, 2-Heq), 3.29 (d, J=6 Hz; 2H, 6-H$_2$), 3.46 (s; 3H, 1-α-OCH$_3$), 3.70–3.85 (m; 1H, 3-H), 3.80 (s; 3H, Aryl-OCH$_3$), 4.22 (dt, J=6 Hz, J=30 Hz; 1 H, 5-H), 4.58 (dd, J=47 Hz, J=4.0 Hz; 1H, 4-H), 4.55 (AB-System; 2H, Aryl-CH$_2$-O), 4.79 (dd, J=4.5 Hz, J=2.5 Hz; 1H, α-1-H), 6.90 and 7.30 (AA'BB'-System; 4H, Aryl-H).

MS (FAB, 3-NBA, LiI): m/e=417 (M$^+$+Li).

EXAMPLE 31

2,4,6-Trideoxy-4(R)-fluoro-3-O-paramethoxybenzyl-6-triphenylphosphonio-α-methyl-D-gulopyranoside iodide (formula XII, R$^{20}$=para-methoxybenzyl, R$^{21}$=methyl)

9.5 g (0.023 mol) of 6-ioduloside from Example 30 and 15 g (0.057 mol) of triphenylphosphine were mixed and stirred at 110° C. for 4 hours. The mixture was then cooled, dissolved in methanol and extracted once with cyclohexane. The methanolic solution was concentrated and purified by chromatography (SiO$_2$, ethyl acetate: methanol=10:1). 12.5 g (0.19 mol)=81% of a pale yellow solid were obtained, $R_f$(product)=0.02, $R_f$ (precursor)=0.79 (cyclohexane:ethyl acetate: 1:1). $R_f$ (product)=0.43, $R_f$ (precursor)=0.98 (CHCl$_3$:CH$_3$OH=4:1). $[\alpha]_D^{20}=+8.5°$ C., c=1.1, CHCl$_3$.

$^1$H-NMR (270 MHz, CDCl$_3$): δ=1.78 (ddd, J=15 Hz, J=5 Hz, J=3 Hz; 1H, 2-Hax), 2.00 (dddd, J=15 Hz, J=5 Hz, J=5 Hz, J=3 Hz; 1H, 2-Heq), 2.58 (s; 3H, α-1-OCH$_3$), 3.60 (dt, J=15.5 Hz, J=J=11.0 Hz; 1 H, 6-Ha), 3.78 (m$_c$; 1H, 3-H), 3.80 (s; 3H, Aryl-OCH$_3$), 4.53 (dd, J=5.0, J=2.3 Hz; 1H, α-1-H), 4.67 (AB-System; 2H, Aryl-CH$_2$O), 4.8–4.6 (m; 1H, 5-H), 5.22 (dt, J=J=15.5 Hz, J=3.5 Hz; 1 H, 6-H$_b$), 5.34 (dd, J=47 Hz, J=4.5 Hz; 1H, 4-H), 6.87 (AA'BB'-System; 4H, Aryl-H), and 7.28 7.60 - (m; 15H, Aryl-H), 7.95.

EXAMPLE 32

4(R)-Fluoro-7-(2-isopropyl-4-parafluorophenyl-6-phenyl-3-pyridyl)-3-O-paramethoxybenzyl-2,4,6,7-tetradeoxy-α-methyl-D-gulohept-6E-enopyranoside (formula XIV, R$^{20}$=para-methoxybenzyl, R$^{21}$=methyl, R=2-isopropyl-4-parafluorophenyl-6-phenyl-3-pyridyl)

18.0 ml of a 1.6 M n-BuLi solution in hexane (0.0288 mol) were added, at −70° C. under argon, to 1.9 ml (1.37 g =0.0136 mol) of diisopropylamine (distilled over LiAlH$_4$) in 400 ml of THF (freshly distilled over LiAlH$_4$). The mixture was allowed to warm to room temperature, stirred for 5 minutes and cooled to −70° C., and 200 ml of absolute hexamethylphosphoric triamide (HMPA) were added. 10.0 g (0.0149 mol) of the phosphonium iodide from Example 31, dissolved in 15 ml of absolute THF, were rapidly added dropwise to this solution. One minute after the addition was complete, a solution of 7.1 g (0.0222 mol) of the pyridine aldehyde from Example 22 was rapidly added dropwise, and the mixture was stirred at this temperature for 30 min. It was then allowed to warm to RT within 45 min. Water was added cautiously, and the mixture was extracted with ether. The organic phase was dried over MgSO$_4$ and concentrated. The product was purified by chromatography on silica gel (200 g Amicon 35–70 μm, cyclohexane:ethyl acetate=19:1). 7.3 g (0.0125 mol=84% of pale yellow oil were obtained, R$_f$=0.42 (toluene:cyclohexane:ethyl acetate=7:2:1), R$_f$=0.36 (cyclohexane:ethyl acetate=4:1).

$^1$H-NMR (270 MHz, CDCl$_3$): δ=1.36 (dd, J=7 Hz, J=2 Hz; 6H, CH(CH$_3$)$_2$, 1.92 (ddd, J=15 Hz, J=5 Hz, J=3 Hz; 1H, 2-Hax), 2.02 (dddd, J=15 Hz, J=5 Hz, J=5 Hz, J=3 Hz; 1H, 2-Heq), 3.37 (s; 3H, α-1-OCH$_3$), 3.49 (hept, J=7 Hz; 1H, CH(CH$_3$)$_2$), 3.78 (dddd, J=10 Hz, J=J=J=4 Hz, 1H, 3-H), 3.82 (s; 3H, Aryl-OCH$_3$), 4.26 (dd, J=46 Hz, J=4 Hz; 1H, 4-H), 4.54 (m$_c$, AB-System; 2H, Aryl-CH$_2$O), 4.57 (dd, J=30 Hz, J=6 Hz; 1H, 5-H), 4.79 (dd, J=4Hz, J=2 Hz; 1 H, α-1-H), 5.55 (dd, J=16 Hz, J=6 Hz; 1H, 6-H), 6.66 (dd, J=16 Hz, J=2 Hz; 1H, 7-H), 6.89 (m$_c$; 2H, Aryl-H), 7.08 (m$_c$; 3 H, Aryl-H), 7.20–7.50 (m; 7H, Aryl-H), 8.12 (m$_c$; 2H, Aryl-H).

MS (DCI, isobutane): m/e=586 (M+H$^+$), 554 (M$^+$—OCH$_3$), 464 (M$^+$—CH$_3$—C$_6$H$_4$—CH$_2$), 316 (3-ethenylpyridinium cation), 121 (CH$_3$O—C$_6$H$_4$CH$_2$+).

EXAMPLE 33

4(R)-Fluoro-7-(2-isopropyl-4-parafluorophenyl-6-phenyl-3-pyridyl)-2,4,6,7-tetradeoxy-D-gulohept-6E-enopyranose (formula XV,
R=2-isopropyl-4-parafluorophenyl-6-phenyl-3-pyridyl)

4.3 g (0.0073 mol) of the D-guloheptenopyranoside from Example 32 were dissolved in 150 ml of acetone and cooled to −20° C., and 150 ml of 27% HCl were added at this temperature. The mixture was then stirred at 0° C. for one hour and at RT for three h. It was then neutralized with solid Na$_2$CO$_3$, while cooling in ice, and the precipitate was filtered off with suction and washed with acetone. The organic phase was concentrated, the residue was taken up in CH$_2$Cl$_2$, and the solution was washed with water, dried over MgSO$_4$ and concentrated. The product was purified by recrystallization from toluene. 2.4 g (0.0053 mol)=73% of white crystals of melting point 180° C. were obtained, R$_f$ (precursor)=0.42, R$_f$ (hemiacetal)=0.15, R$_f$ (product)=0.04 (toluene:cyclohexane:ethyl acetate=7:2:1).

$^1$H-NMR (270 MHz, CDCl$_3$): δ=1.35 (d, J=7 Hz; 6H, CH(CH$_3$)$_2$), 1.92 (d (br), J=15 Hz; 1H, 2-Hax), 2.11 (d (br), J=15 Hz; 1 H 2-Heq), 3.40 (m; 1H, OH), 3.49 (hept., J=7 Hz; 1H, CH(CH$_3$)$_2$), 4.10 (m; 1H, 3-H) 4.21 (dd, J=47 Hz, J=4 Hz; 1H, 4-H), 4.79 (dd, J=32 Hz, J=6 Hz; 1H, 5-H), 5.43 (s (br); 1H, 1-H), 5.57 (dd, J=16 Hz, J=6 Hz, 1H, 6-H), 6.68 (d, J=16 Hz; 1H, 7-H), 7.05–7.5 (m; 8H, Aryl-H), 8.10 (m; 2H, Aryl-H).

MS (DCI, isobutane): m/e=452 (M+H$^+$), 434 (M$^+$-OH), 316 (2-isopropyl-3-ethenyl-4-p-fluorophenyl-6-phenylpyridinium cation).

EXAMPLE 34

3(S),5(R)-Dihydorxy-4(R)-fluoro-7-(2-isopropyl-4-parafluorophenyl-6-phenyl-3-pyridyl)hept-6E-enoic acid lactone (formula I, X-Y=E—CH=CH, R=2-isopropyl-4-parafluorophenyl-6-phenyl-3-pyridyl).

7.6 g (0.017 mol) of the hemiacetal from Example 33, 19 g (0.085 mol) of N-iodosuccinimide and 12.7 g (0.034 mol) of tetrabutylammonium iodide in 380 ml of absolute CH$_2$Cl$_2$ were reacted in accordance with Example 11; reaction time 6 hours. 6.2 g (0.014 mol)=81% of white crystalline product of melting point 145°–147° C. were obtained. R$_f$(product)=0.36, R$_f$(precursor)=0.38 (cyclohexane:ethyl acetate=1:1).

$^1$H-NMR (270 MHz, CDCl$_3$): δ=1.36 (d, J=7 Hz; 3H, CH(CH$_3$), 1.39 (d, J=7 Hz; 3H, CH(CH$_3$), 2.24 (d, J=4 Hz; 1H, OH), 2.66 (ddd, J=18 Hz, J=3 Hz, J=3 Hz; 1H, 2-Hax), 2.93 (ddd, J=18 Hz, J=5 Hz, J=4 Hz; 1H, 2-Heq), 3.46 (hept., J=7 Hz; 1H, CH(CH$_3$)$_2$), 4.37 (m$_c$; 1H, 3-H), 4.44 (ddd, J=52 Hz, J=4.5 Hz, J=1.5 Hz; 1H, 4-H), 5.15 (dddd, J=30 Hz, J=7 Hz, J=1 Hz, J=1 Hz; 1H, 5-H), 5.58 (dd, J=16 Hz, J=7 Hz; 1H, 6-H), 6.79 (dd, J=16 Hz, J=1 Hz; 1H, 7-H), 7.12 (m; 2H, Aryl-H), 7.23–7.5 (m; 6H, Aryl-H), 8.10 (m; 2H, Aryl-H).

MS (DCI, isobutane): m/e=450 (M+H$^+$), 432 (M$^+$—OH), 405 M$^+$—CO$_2$), 316.

UV (CH$_2$Cl$_2$): λ$_{max}$ (lg E)=254 (4.40), 300 nm (4.15)sh.

$[α]_D^{20}$=+22.3°, c=1, CHCl$_3$.

$^{19}$F-NMR (339 MHz, CDCl$_3$, CFCl$_3$ int. Standard): δ=−114.77 (m; 1F, Aryl-F), −203.71 (ddddd, J=46 Hz, J=30 Hz, J=6 Hz, J=6 Hz, H=3 Hz; 1 F, 4-(R)-F).

EXAMPLE 35

Sodium 3(S),5(R)-dihydroxy-4(R)-fluoro-7-(2-isopropyl-4-para-fluorophenyl-6-phenyl-3-pyridyl)hept-6E-enoate (formula II, X-Y=E—CH=CH, R=2-isopropyl-4-para-fluorophenyl-6-phenyl-3-pyridyl); CO$_2$Na in place of CO$_2$H)

17.4 mg (3.9×10$^{-5}$ mol) of the lactone from Example 34 were dissolved in 3.9 ml of analytical grade ethanol, 39 μl of 1N NaOH were added, and the mixture was stirred at RT for one hour. It was then cautiously concentrated (rotary evaporator), and the residue was taken up in 3.9 ml of water. The solution prepared in this way was used for the enzyme assay (liver homogenate) and for investigating the inhibition of biosynthesis in HEP-G2 cells. TLC analysis: R$_f$ (lactone)=0.79, R$_f$ (Na salt)=0.16 (CHCl$_3$:CH$_3$OH=4:1).

EXAMPLE 36

3(S),5(R)-dihydroxy-4(R)-fluoro-7-(2-isopropyl-4-parafluorophenyl-6-phenyl-3-pyridyl)heptanoic acid lactone (formula I, X-Y=CH$_2$—CH$_2$, R=2-isopropyl-4-parafluorophenyl-6-phenyl-3-pyridyl)

0.5 g of catalyst (10% Pd/C) was prehydrogenated in ethyl acetate for 30 min. 0.100 g (0.22×10$^{-3}$ mol) of lactone from Example 34 was added, and the mixture was hydrogenated in a shaken vessel until 5 ml of H$_2$ had been absorbed. The catalyst was then removed by filtration, washing the filter cake with ethyl acetate and the filtrate was dried (MgSO$_4$) and concentrated. 0.098 g (2.17×10$^{-4}$ mol)=98% of colorless oil was obtained. R$_f$ (product)=0.33, R$_f$ (precursor)=0.33 (cyclohexane:ethyl acetate=1:1).

$^1$H-NMR (270 MHz, CDCl$_3$):δ=1.39 (d, J=7 Hz; 3H, CH(C$\underline{H}_3$)$_2$), 1.42 (d, J=7 Hz; 3H, CH(C$\underline{H}_3$)$_2$), 1.70–1.88 (m; 1H, 6-H), 1.92–2.08 (m; 1H, 6-H), 2.18 (d, J=5 Hz; 1H, OH), 2.59 (ddd, J=18 Hz, J=3 Hz, J=3 Hz; 1H, 2-H), 2.70 (m; 1H, 7-H), 2.88 (ddd, J=18 Hz, J=5 Hz, J=4 Hz; 1H, 2-H), 2.89 (m; 1H, 7-H), 3.37 (hept., J=7 Hz; 1H, CH(CH$_3$)$_2$), 4.30–4.55 (m; 3H, 3-H, 4-H, 5-H), 7.10–7.50 (m; 8H, Aryl-H), 8.10 (m; 2H, Aryl-H).

MS (DCI, isobutane): m/e=452 (M+H$^+$), 318 (2-isopropyl-3-ethyl-4-fluorophenyl-6-phenylpyridinium cation).

EXAMPLE 37

5-Formyl-4-isopropyl-6-parafluorophenyl-2-phenyl-1,3-diazine (formula XIIIb, A=N, R$^{10}$=isopropyl, R$^{11}$=parafluorophenyl, R$^{12}$=phenyl)

The appropriately substituted pyrimidine-5-aldehyde was prepared from the corresponding ethyl ester by reduction (CH$_2$Cl$_2$, −78° C., Ar, 3 eq DIBAH, 2 h −78°, 0.5 h, 0° C., 77% yield) and subsequent oxidation (CH$_2$Cl$_2$, PCC, 3 h RT, chromatography, 87% yield).

White solid, melting point 119°–121° C.

$^1$H-NMR (60 MHz, CDCl$_3$): δ=1.4 (d, J=7 Hz; 6H, CH(C$\underline{H}_3$)$_3$), 4.0 (hept., J=7 Hz; 1H CH(C$\underline{H}_3$)$_3$), 7.2–8.0 (m; 6H, Aryl-H), 8.6 (m$_c$; 2H, Aryl-H), 10.1 (s; 1H, CHO).

The starting material for the ethyl pyrimidine-5-carboxylate was commercially available benzamidine hydrochloride, together with 4-carboethoxy-2-methyl-5-parafluorophenylpent-4-en-3-one which was obtained by aldol condensation of ethyl isobutyrylacetate and parafluorobenzaldehyde. The components were reacted in accordance with the procedure of E. F. Silversmith, J. Org. Chem. 27 (1962) 4090, and the resulting dihydropyrimidine was aromatized by heating with DDQ or MnO$_2$ in toluene.

EXAMPLE 38

3(S),5(R)-dihydroxy-4(R)-fluoro-7-[6-parafluorophenyl-4-isopropyl-2-phenyl-1,3-diazin-5-yl]hept-6E-enoic acid lactone (formula I, X-Y=E—CH=CH, R=6-parafluorophenyl-4-isopropyl-2-phenyl-1,3-diazin-5-yl)

0.75 g (0.0011 mol) of the phosphonium iodide from Example 31, 40 ml of THF, 1.2 ml of 1.6 M n-BuLi, 0.13 ml of diisopropylamine, 20 ml of HMPA and 0.72 g (0.0025 mol) of the 1,3-diazine aldehyde from Example 37 were reacted in a Wittig reaction as in Example 32, and the further conversion to the lactone was then carried out as in Examples 33 and 34. 194 mg (0.43×10$^{-3}$ mol)=39% of lactone were obtained, R$_f$=0.35 cyclohexane:ethyl acetate=1:1).

$^1$H-NMR (270 MHz, CDCl$_3$): δ=1.34 (d, J=7 Hz; 3H, CH(CH$_3$)$_2$), 1.38 (d, J=7 Hz; 3 H(CH$_3$)$_2$), 2.69 (ddd, J=18 Hz, J=3 Hz, J=3 Hz; 1H, 2-H), 2.95 (ddd, J=18 Hz, J=5 Hz, J=4 Hz; 1H, 2-H), 3.43 (hept, J=7 Hz; 1H, CH(C$\underline{H}_3$)$_2$), 4,41 (m; 1H, 3-H), 4.55 (ddd, J=47 hz, J=4 Hz, J∼1 Hz; 1H, 4-H), 5.22 (dddd, J=30 Hz, J=7 Hz, J=J∼1 Hz; 1H, 5-H), 5.71 (dd, J=16 Hz, J=7 Hz; 1H, 6-H), 6.89 (dd, J=16 Hz, J∼1 Hz; 1H, 7-H), 7.12 (m$_c$; 2H, Aryl-H), 7.35 (m$_c$; 1H, Aryl-H), 7.49 (m$_c$; 2H, Aryl-H) 7.71 (m$_c$; 2H, Aryl-H), 8.58 (m$_c$; 2H, Aryl-H).

MS (DCI, isobutane): m/e=451 (M+H$^+$), 433 (M$^+$-OH), 406 (M$^+$-CO$_2$), 363 (406-CHMe$_2$), 317 (5-ethenyl-4-isopropyl-6-para-fluorophenyl-2-phenyl-1,3-diazine cation).

EXAMPLE 39

3(S),5(R)-Dihydroxy-4(R)-fluoro-7-[2-isopropyl-4-phenyl-6-parafluorophenylphenyl]hept-6E-enoic acid lactone (formula I, X-Y=E—CH=CH, R=2-isopropyl-4-phenyl-6-parafluorophenylphenyl).

1.0 g (0.0015 mol) of the phosphonium iodide from Example 31 was reacted with 1.9 ml of 1.6 M n-BuLi, 0.9 ml of diisopropylamine, 40 ml of THF and 20 ml of HMPA together with 0.6 g (0.0019 mol) of the aldehyde from Example 24 in a Wittig reaction, followed by hydrolysis of protective groups and oxidation of the hemiacetal as in Examples 32, 33 and 34. 222 mg (0.0005 mol)=33% of lactone were obtained, R$_f$=0.42 (cyclohexane:ethyl acetate=1:1).

$^1$H-NMR (270 MHz, CDCl$_3$): δ=1.31 (d, J=7 Hz; 3H, CH(CH$_3$)$_2$), 1.33 (d, J=7 Hz; 3H, CH(C$\underline{H}_3$)$_2$), 1.62 (ddd, J=18 Hz, J=3 Hz, J=3 Hz; 1H, 2-H), 2.91 (ddd, J=18 Hz, J=5 Hz, J=4 Hz; 1H, 2-H), 3.32 (hept, J=7 Hz; 1H, C$\underline{H}$Me$_2$), 4.30 (m; 1H, 3-H), 4.39 (ddd, J=47 Hz, J=4 Hz, J=1 Hz; 1H, 4-H), 5.11 (dd, J=28 Hz, J=6 Hz; 1H, 5-H), 5.53 (dd, J=16 Hz, J=6 Hz; 6-H), 6.80 (d, J=16 Hz; 1 H, 7-H), 7.05–7.65 (m; 11H, Aryl-H).

EXAMPLE 40

3(S),5(R)-Dihydroxy-4(R)-fluoro-7-(2,4-dimethyl-6-parafluorophenylphenyl)hept-6E-enoic acid lactone (formula I, X-Y=E—CH=CH, R=2,4-dimethyl-6-p-fluorophenylphenyl)

1.0 g (0.0015 mol) of the phosphonium iodide from Example 31 was reacted with 1.85 ml of 1.6 M n-BuLi, 0.9 ml of diisopropylamine, 40 ml of THF, 20 ml of HMPA together with 0.69 g (0.003 mol) of the substituted benzaldehyde from Example 23 in a Wittig reaction, followed by hydrolysis of protective groups and oxidation of the hemiacetal as in Examples 32, 33 and 34. 0.193 g (0.00054 mol)=36% of lactone was obtained, R$_f$=0.44 (cyclohexane:ethyl acetate=1:1).

$^1H$-NMR (60 MHz, $CDCl_3$): δ=2.3 (s; 3H, Aryl-$CH_3$), 2.6 (s; 3H, Aryl-$CH_3$), 2.6 (m; 1H, 2-H), 2.09 (d, J=18 Hz; 1H, 2-H), 4.3 (m; 1H, 3-H), 4.4 (d, J=46 Hz; 1H, 4-H), 5.1 (dd, J=30 Hz, J=6 Hz; 1H, 5-H), 5.5 (dd, J=18 Hz, J=6 Hz; 1H, 6-H), 6.8 (d, J=18 Hz; 1H, 7-H), 7.0–7.7 (m; 6 H, Aryl-H).

EXAMPLE 41

Sodium 3(S),5(R)-dihydroxy-4(R)-fluoro-7-(2-isopropyl-4-parafluorophenyl-6-phenyl-3-pyridyl)heptanoate (formula II, X-Y=$CH_2$—$CH_2$, R=2-isopropyl-4-parafluorophenyl-6-phenyl-3-pyridyl)

The compound was prepared as a $10^{-2}$ molar aqueous solution in accordance with Example 35 from the lactone of Example 36.

EXAMPLE 42

Sodium 3(S),5(R)-dihydroxy-4(R)-fluoro-7-[6-parafluorophenyl-4-isopropyl-2-phenyl-1,3-diazin-5-yl]hept-6E-enoate (formula II, X-Y=E—CH=CH, R=6-parafluorophenyl-4-isopropyl-2-phenyl-1,3-diazin-5-yl)

The compound was prepared in accordance with Example 35 from the lactone of Example 38 as a $10^{-2}$ molar aqueous solution.

EXAMPLE 43

Sodium 3(S),5(R)-dihydroxy-4(R)-fluoro-7[2-isopropyl-4-phenyl-6-parafluorophenylphenyl]hept-6E-enoate (formula II, X-Y=E—CH=CH, R=2-isopropyl-4-phenyl-6-p-fluorophenylphenyl)

The compound was prepared in accordance with Example 35 from the lactone of Example 39 as a $10^{-2}$ molar aqueous solution.

EXAMPLE 44

Sodium 3(S),5(R)-dihydroxy-4(R)-fluoro-7[2,4-dimethyl-6-parafluorophenylphenyl]hept-6E-enoate (formula II, X-Y=E—CH=CH, R=2,4-dimethyl-6-p-fluorophenylphenyl)

The compound was prepared from the lactone (Example 40) in accordance with Example 35 as a $10^{-2}$ molar aqueous solution.

We claim:

1. A 3-demethyl-4-fluoromevalonic acid derivative of the formula I

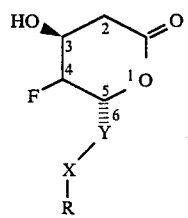

and the corresponding free dihydroxy carboxylic acid of the formula II

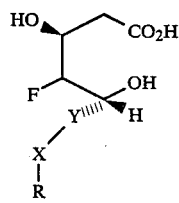

in which
Y-X-R denotes
$R^8$ and $R^9$ denote hydrogen, halogen, trifluoromethyl, or alkyl or alkoxy, each having 1 to 6 carbon atoms, the group of the formula V

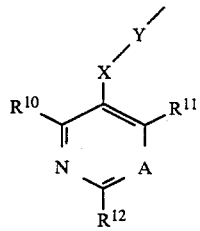

in which
X-Y is equal to CH=CH or $CH_2$—$CH_2$
A is equal to CH and
$R^{10}$ denotes H, straight-chain $C_1$-$C_4$-alkyl, branched $C_3$-$C_6$-alkyl, trifluoromethyl or perfluoroisopropyl,
$R^{11}$ denotes H, straight-chain $C_1$-$C_4$-alkyl, branched $C_3$-$C_6$-alkyl, cycloalkyl having 5–8 ring carbon atoms, phenyl which can be substituted 1 or 2 times by straight-chain $C_1$-$C_3$-alkyl, $C_1$-$C_3$-alkoxy, halogen or by trifluoromethyl;
$R^{12}$ denotes H, straight-chain $C_1$-$C_4$-alkyl, branched $C_3$-$C_6$-alkyl, cycloalkyl having 5–8 ring carbon atoms, phenyl which can in turn be substituted 1 or 2 times by straight-chain $C_1$-$C_3$-alkyl, trifluoromethyl, hydroxyl or by halogen.

2. A pharmaceutical product containing an effective amount of a compound as claimed in claim 1 in combination with a pharmaceutically acceptable carrier.

3. A method for the prophylaxis and therapy of hypercholesterolemia comprising the step of administering to a host an amount of the compound of claim 1 effective to prevent or treat hypercholesterolemia.

* * * * *

EXAMPLE 36

3(S),5(R)-dihydroxy-4(R)-fluoro-7-(2-isopropyl-4-parafluorophenyl-6-phenyl-3-pyridyl)heptanoic acid lactone (formula I, X-Y=CH$_2$—CH$_2$, R=2-isopropyl-4-parafluorophenyl-6-phenyl-3-pyridyl)

0.5 g of catalyst (10% Pd/C) was prehydrogenated in ethyl acetate for 30 min. 0.100 g (0.22×10$^{-3}$ mol) of lactone from Example 34 was added, and the mixture was hydrogenated in a shaken vessel until 5 ml of H$_2$ had been absorbed. The catalyst was then removed by filtration, washing the filter cake with ethyl acetate and the filtrate was dried (MgSO$_4$) and concentrated. 0.098 g (2.17×10$^{-4}$ mol)=98% of colorless oil was obtained. R$_f$ (product)=0.33, R$_f$ (precursor)=0.33 (cyclohexane:ethyl acetate=1:1).

$^1$H-NMR (270 MHz, CDCl$_3$):δ=1.39 (d, J=7 Hz; 3H, CH(C$\underline{H}$$_3$)$_2$), 1.42 (d, J=7 Hz; 3H, CH(C$\underline{H}$$_3$)$_2$), 1.70–1.88 (m; 1H, 6-H), 1.92–2.08 (m; 1H, 6-H), 2.18 (d, J=5 Hz; 1H, OH), 2.59 (ddd, J=18 Hz, J=3 Hz, J=3 Hz; 1H, 2-H), 2.70 (m; 1H, 7-H), 2.88 (ddd, J=18 Hz, J=5 Hz, J=4 Hz; 1H, 2-H), 2.89 (m; 1H, 7-H), 3.37 (hept., J=7 Hz; 1H, CH(CH$_3$)$_2$), 4.30–4.55 (m; 3H, 3-H, 4-H, 5-H), 7.10–7.50 (m; 8H, Aryl-H), 8.10 (m; 2H, Aryl-H).

MS (DCI, isobutane): m/e=452 (M+H$^+$), 318 (2-isopropyl-3-ethyl-4-fluorophenyl-6-phenylpyridinium cation).

EXAMPLE 37

5-Formyl-4-isopropyl-6-parafluorophenyl-2-phenyl-1,3-diazine (formula XIIIb, A=N, R$^{10}$=isopropyl, R$^{11}$=parafluorophenyl, R$^{12}$=phenyl)

The appropriately substituted pyrimidine-5-aldehyde was prepared from the corresponding ethyl ester by reduction (CH$_2$Cl$_2$, −78° C., Ar, 3 eq DIBAH, 2 h −78°, 0.5 h, 0° C., 77% yield) and subsequent oxidation (CH$_2$Cl$_2$, PCC, 3 h RT, chromatography, 87% yield).

White solid, melting point 119°–121° C.

$^1$H-NMR (60 MHz, CDCl$_3$): δ=1.4 (d, J=7 Hz; 6H, CH(C$\underline{H}$$_3$)$_3$), 4.0 (hept., J=7 Hz; 1H CH(C$\underline{H}$$_3$)$_3$), 7.2–8.0 (m; 6H, Aryl-H), 8.6 (m$_c$; 2H, Aryl-H), 10.1 (s; 1H, CHO).

The starting material for the ethyl pyrimidine-5-carboxylate was commercially available benzamidine hydrochloride, together with 4-carboethoxy-2-methyl-5-parafluorophenylpent-4-en-3-one which was obtained by aldol condensation of ethyl isobutyrylacetate and parafluorobenzaldehyde. The components were reacted in accordance with the procedure of E. F. Silversmith, J. Org. Chem. 27 (1962) 4090, and the resulting dihydropyrimidine was aromatized by heating with DDQ or MnO$_2$ in toluene.

EXAMPLE 38

3(S),5(R)-dihydroxy-4(R)-fluoro-7-[6-parafluorophenyl-4-isopropyl-2-phenyl-1,3-diazin-5-yl]hept-6E-enoic acid lactone (formula I, X-Y=E—CH=CH, R=6-parafluorophenyl-4-isopropyl-2-phenyl-1,3-diazin-5-yl)

0.75 g (0.0011 mol) of the phosphonium iodide from Example 31, 40 ml of THF, 1.2 ml of 1.6 M n-BuLi, 0.13 ml of diisopropylamine, 20 ml of HMPA and 0.72 g (0.0025 mol) of the 1,3-diazine aldehyde from Example 37 were reacted in a Wittig reaction as in Example 32, and the further conversion to the lactone was then carried out as in Examples 33 and 34. 194 mg (0.43×10$^{-3}$ mol)=39% of lactone were obtained, R$_f$=0.35 cyclohexane:ethyl acetate=1:1).

$^1$H-NMR (270 MHz, CDCl$_3$): δ=1.34 (d, J=7 Hz; 3H, CH(CH$_3$)$_2$), 1.38 (d, J=7 Hz; 3 H(CH$_3$)$_2$), 2.69 (ddd, J=18 Hz, J=3 Hz, J=3 Hz; 1H, 2-H), 2.95 (ddd, J=18 Hz, J=5 Hz, J=4 Hz; 1H, 2-H), 3.43 (hept, J=7 Hz; 1H, CH(C$\underline{H}$$_3$)$_2$), 4.41 (m; 1H, 3-H), 4.55 (ddd, J=47 hz, J=4 Hz, J~1 Hz; 1H, 4-H), 5.22 (dddd, J=30 Hz, J=7 Hz, J=J~1 Hz; 1H, 5-H), 5.71 (dd, J=16 Hz, J=7 Hz; 1H, 6-H), 6.89 (dd, J=16 Hz, J~1 Hz; 1H, 7-H), 7.12 (m$_c$; 2H, Aryl-H), 7.35 (m$_c$; 1H, Aryl-H), 7.49 (m$_c$; 2H, Aryl-H) 7.71 (m$_c$; 2H, Aryl-H), 8.58 (m$_c$; 2H, Aryl-H).

MS (DCI, isobutane): m/e=451 (M+H$^+$), 433 (M$^+$-OH), 406 (M$^+$-CO$_2$), 363 (406-CHMe$_2$), 317 (5-ethenyl-4-isopropyl-6-para-fluorophenyl-2-phenyl-1,3-diazine cation).

EXAMPLE 39

3(S),5(R)-Dihydroxy-4(R)-fluoro-7-[2-isopropyl-4-phenyl-6-parafluorophenylphenyl]hept-6E-enoic acid lactone (formula I, X-Y=E—CH=CH, R=2-isopropyl-4-phenyl-6-parafluorophenylphenyl).

1.0 g (0.0015 mol) of the phosphonium iodide from Example 31 was reacted with 1.9 ml of 1.6 M n-BuLi, 0.9 ml of diisopropylamine, 40 ml of THF and 20 ml of HMPA together with 0.6 g (0.0019 mol) of the aldehyde from Example 24 in a Wittig reaction, followed by hydrolysis of protective groups and oxidation of the hemiacetal as in Examples 32, 33 and 34. 222 mg (0.0005 mol)=33% of lactone were obtained, R$_f$=0.42 (cyclohexane:ethyl acetate=1:1).

$^1$H-NMR (270 MHz, CDCl$_3$): δ=1.31 (d, J=7 Hz; 3H, CH(CH$_3$)$_2$), 1.33 (d, J=7 Hz; 3H, CH(C$\underline{H}$$_3$)$_2$), 1.62 (ddd, J=18 Hz, J=3 Hz, J=3 Hz; 1H, 2-H), 2.91 (ddd, J=18 Hz, J=5 Hz, J=4 Hz; 1H, 2-H), 3.32 (hept, J=7 Hz; 1H, C$\underline{H}$Me$_2$), 4.30 (m; 1H, 3-H), 4.39 (ddd, J=47 Hz, J=4 Hz, J=1 Hz; 1H, 4-H), 5.11 (dd, J=28 Hz, J=6 Hz; 1H, 5-H), 5.53 (dd, J=16 Hz, J=6 Hz; 6-H), 6.80 (d, J=16 Hz; 1 H, 7-H), 7.05–7.65 (m; 11H, Aryl-H).

EXAMPLE 40

3(S),5(R)-Dihydroxy-4(R)-fluoro-7-(2,4-dimethyl-6-parafluorophenylphenyl)hept-6E-enoic acid lactone (formula I, X-Y=E—CH=CH, R=2,4-dimethyl-6-p-fluorophenylphenyl)

1.0 g (0.0015 mol) of the phosphonium iodide from Example 31 was reacted with 1.85 ml of 1.6 M n-BuLi, 0.9 ml of diisopropylamine, 40 ml of THF, 20 ml of HMPA together with 0.69 g (0.003 mol) of the substituted benzaldehyde from Example 23 in a Wittig reaction, followed by hydrolysis of protective groups and oxidation of the hemiacetal as in Examples 32, 33 and 34. 0.193 g (0.00054 mol)=36% of lactone was obtained, R$_f$=0.44 (cyclohexane:ethyl acetate=1:1).

$^1$H-NMR (60 MHz, CDCl$_3$): δ=2.3 (s; 3H, Aryl-CH$_3$), 2.6 (s; 3H, Aryl-CH$_3$), 2.6 (m; 1H, 2-H), 2.09 (d, J=18 Hz; 1H, 2-H), 4.3 (m; 1H, 3-H), 4.4 (d, J=46 Hz; 1H, 4-H), 5.1 (dd, J=30 Hz, J=6 Hz; 1H, 5-H), 5.5 (dd, J=18 Hz, J=6 Hz; 1H, 6-H), 6.8 (d, J=18 Hz; 1H, 7-H), 7.0–7.7 (m; 6 H, Aryl-H).

EXAMPLE 41

Sodium 3(S),5(R)-dihydroxy-4(R)-fluoro-7-(2-isopropyl-4-parafluorophenyl-6-phenyl-3-pyridyl)heptanoate (formula II, X-Y=CH$_2$—CH$_2$, R=2-isopropyl-4-parafluorophenyl-6-phenyl-3-pyridyl)

The compound was prepared as a 10$^{-2}$ molar aqueous solution in accordance with Example 35 from the lactone of Example 36.

EXAMPLE 42

Sodium 3(S),5(R)-dihydroxy-4(R)-fluoro-7-[6-parafluorophenyl-4-isopropyl-2-phenyl-1,3-diazin-5-yl]hept-6E-enoate (formula II, X-Y=E—CH=CH, R=6-parafluorophenyl-4-isopropyl-2-phenyl-1,3-diazin-5-yl)

The compound was prepared in accordance with Example 35 from the lactone of Example 38 as a 10$^{-2}$ molar aqueous solution.

EXAMPLE 43

Sodium 3(S),5(R)-dihydroxy-4(R)-fluoro-7[2-isopropyl-4-phenyl-6-parafluorophenylphenyl]hept-6E-enoate (formula II, X-Y=E—CH=CH, R=2-isopropyl-4-phenyl-6-p-fluorophenylphenyl)

The compound was prepared in accordance with Example 35 from the lactone of Example 39 as a 10$^{-2}$ molar aqueous solution.

EXAMPLE 44

Sodium 3(S),5(R)-dihydroxy-4(R)-fluoro-7[2,4-dimethyl-6-parafluorophenylphenyl]hept-6E-enoate (formula II, X-Y=E—CH=CH, R=2,4-dimethyl-6-p-fluorophenylphenyl)

The compound was prepared from the lactone (Example 40) in accordance with Example 35 as a 10$^{-2}$ molar aqueous solution.

We claim:

1. A 3-demethyl-4-fluoromevalonic acid derivative of the formula I

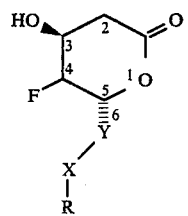

and the corresponding free dihydroxy carboxylic acid of the formula II

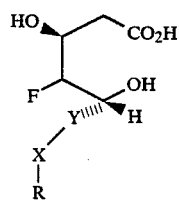

in which

Y-X-R denotes

R$^8$ and R$^9$ denote hydrogen, halogen, trifluoromethyl, or alkyl or alkoxy, each having 1 to 6 carbon atoms, the group of the formula V

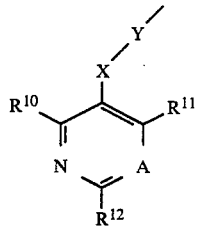

in which

X-Y is equal to CH=CH or CH$_2$—CH$_2$

A is equal to CH and

R$^{10}$ denotes H, straight-chain C$_1$-C$_4$-alkyl, branched C$_3$-C$_6$-alkyl, trifluoromethyl or perfluoroisopropyl, R$^{11}$ denotes H, straight-chain C$_1$-C$_4$-alkyl, branched C$_3$-C$_6$-alkyl, cycloalkyl having 5-8 ring carbon atoms, phenyl which can be substituted 1 or 2 times by straight-chain C$_1$-C$_3$-alkyl, C$_1$-C$_3$-alkoxy, halogen or by trifluoromethyl;

R$^{12}$ denotes H, straight-chain C$_1$-C$_4$-alkyl, branched C$_3$-C$_6$-alkyl, cycloalkyl having 5-8 ring carbon atoms, phenyl which can in turn be substituted 1 or 2 times by straight-chain C$_1$-C$_3$-alkyl, trifluoromethyl, hydroxyl or by halogen.

2. A pharmaceutical product containing an effective amount of a compound as claimed in claim 1 in combination with a pharmaceutically acceptable carrier.

3. A method for the prophylaxis and therapy of hypercholesterolemia comprising the step of administering to a host an amount of the compound of claim 1 effective to prevent or treat hypercholesterolemia.

* * * * *